United States Patent
Addington

(10) Patent No.: US 9,861,459 B2
(45) Date of Patent: Jan. 9, 2018

(54) TOOTHBRUSH AND METHOD FOR PROPER BRUSHING OF TEETH AND GUMS IN THE DIRECTION OF GUM GROWTH OPTIONALLY WITH AN ATTACHED CAMERA

(71) Applicant: Raymond Addington, Atlanta, GA (US)

(72) Inventor: Raymond Addington, Atlanta, GA (US)

( * ) Notice: Subject to any disclaimer, the term of this patent is extended or adjusted under 35 U.S.C. 154(b) by 0 days.

(21) Appl. No.: 15/379,601

(22) Filed: Dec. 15, 2016

(65) Prior Publication Data

US 2017/0095320 A1    Apr. 6, 2017

Related U.S. Application Data

(63) Continuation-in-part of application No. 14/824,124, filed on Aug. 12, 2015, and a continuation-in-part of
(Continued)

(51) Int. Cl.
*A61C 17/22* (2006.01)
*A46B 9/04* (2006.01)
(Continued)

(52) U.S. Cl.
CPC .......... *A61C 17/221* (2013.01); *A46B 5/0095* (2013.01); *A46B 9/04* (2013.01);
(Continued)

(58) Field of Classification Search
CPC ... A61B 1/24; A61B 1/00009; A61B 1/00018; A61B 1/005; A61B 1/05; A61B 1/0676; A46B 5/0095; A46B 9/04; A46B 15/0016
See application file for complete search history.

(56) References Cited

U.S. PATENT DOCUMENTS 4,335,480 A    6/1982   Liu
5,604,560 A    2/1997   Kaneda
(Continued)

FOREIGN PATENT DOCUMENTS

AU    2013101537 A4   12/2013
KR    2016028921 A    3/2016

*Primary Examiner* — Shay Karls
(74) *Attorney, Agent, or Firm* — Laurence P. Colton; Smith Tempel Blaha LLC

(57) ABSTRACT

This toothbrush is intended to create healthy gums while cleaning teeth. This toothbrush with its unique combination of bush geometry, specific rotational directions, and brush movement from gums to teeth crowns, will not loosen gums and will correctly position gums as the brush rotational motion and brush movement is always in the direction of gum growth, from gums to teeth crowns. All present toothbrushes, electric and manual on the market, tend to loosen gums as they brush across the direction of gum growth causing loose gums, receding gums, sensitive teeth, gum-line cavities, diseases as gingivitis, loss of teeth. When a dentist and/or hygienist clean under gums, or when a dentist does gum-line fillings, tooth extractions, tooth implants, and receding gum repair, gums need correct alignment to be maintained for a period of time while gums reattach. This toothbrush will be the only brush on the market capable of maintaining gum alignment for a period of time while gums reattach, avoiding tooth problems listed above. With a camera attached, gums can be viewed to insure correct gum positioning as well as spot cleaning teeth. The viewing device uses a type of cell phone most buyers already will have.

15 Claims, 18 Drawing Sheets

Related U.S. Application Data application No. 15/185,246, filed on Jun. 17, 2016, which is a continuation-in-part of application No. 14/824,124, filed on Aug. 12, 2015, which is a continuation-in-part of application No. 14/121,521, filed on Sep. 15, 2014.

(51) Int. Cl.
*A46B 5/00* (2006.01)
*A61C 17/26* (2006.01)
*A46B 15/00* (2006.01)
*A61B 1/247* (2006.01)
*A61B 1/05* (2006.01)
*A61B 1/06* (2006.01)
*A61B 1/00* (2006.01)

(52) U.S. Cl.
CPC ...... *A46B 15/0022* (2013.01); *A46B 15/0036* (2013.01); *A61B 1/00009* (2013.01); *A61B 1/00195* (2013.01); *A61B 1/05* (2013.01); *A61B 1/0684* (2013.01); *A61B 1/247* (2013.01); *A61C 17/222* (2013.01); *A61C 17/225* (2013.01); *A61C 17/26* (2013.01)

(56) References Cited

U.S. PATENT DOCUMENTS

| | | |
|---|---|---|
| D687,227 S | 8/2013 | Hill |
| 8,904,588 B2 | 12/2014 | Taub |
| 9,332,165 B1 | 5/2016 | Russell |

TOOTHBRUSH AND METHOD FOR PROPER BRUSHING OF TEETH AND GUMS IN THE DIRECTION OF GUM GROWTH OPTIONALLY WITH AN ATTACHED CAMERA

STATEMENT OF RELATED APPLICATIONS

This patent application claims the benefit of U.S. patent application Ser. No. 14/824,124 having a filing date of 12 Aug. 2015, which claims the benefit of U.S. patent application Ser. No. 14/121,521 having a filing date of 15 Sep. 2014. This patent application also claims the benefit of U.S. patent application Ser. No. 15/185,246 having a filing date of 17 Jun. 2016, which claims the benefit of U.S. patent application Ser. No. 14/824,124 having a filing date of 12 Aug. 2015, which claims the benefit of U.S. patent application Ser. No. 14/121,521 having a filing date of 15 Sep. 2014.

BACKGROUND OF THE INVENTION

Field of the Invention

The present invention generally relates to the field of toothbrushes designed for a tooth and gum brushing technique that will not loosen or lift the gums during use as the toothbrush brushes in the direction of gum growth. More specifically, the present invention relates to the field of toothbrushes for tooth and gum brushing and tooth and gum health by having a unique combination of brush geometry, of specific brush rotational direction and brush movement from gums to the crowns of the teeth in the direction of gum growth. This combination will not loosen gums.

Current toothbrushes, manual and electric on the market, tend to loosen gums as they brush across the direction of gum growth causing receding gums, sensitive teeth, gum line cavities, and inviting gingivitis. Thus, the present invention relates to the field of toothbrushes having, a rotating bristle assembly, and a reversible rotational direction so as to implement a brushing technique having the brush rotate in a direction from the gum towards the crown of the tooth, and regardless of the specific tooth being brushed, which is in the direction of gum growth so as to not loosen or lift the gums and to improve gum health.

The present invention further relates to the field of video capable electric toothbrushes for proper tooth and gum brushing that will not loosen or lift the gums during use as the toothbrush brushes in the direction of gum growth and will allow the user to view the interior of the mouth while brushing.

Prior Art

Presently available electric toothbrushes have changed dramatically since the manual toothbrushes. These electric toothbrushes typically have a battery and a battery-powered motors to oscillate in circle directions the bristle bundle over teeth and gums, or to rotate continuously in one circular direction the bristle bundle over teeth and gums, or to cycle in a back and forth motion the bristle bundle over teeth and gums, or to vibrate bristle bundles over teeth and gums. Current commercially available electric toothbrushes fail to create proper tooth and gum brushing and/or dental prophylaxis procedure. All changes in types of toothbrushes from manual to electric brushes have not created an improvement in the health of teeth and gums.

All toothbrushes on the market interfere with the periodontal margin by brushing across the direction of gum growth causing loose gums accompanied by tooth and receding gums, sensitive teeth, loose teeth, gum line cavities, diseases such as gingivitis, and loss of teeth. To make matters worse, current commercially available electric toothbrushes actually work against recreating the proper tooth and gum brushing and/or dental prophylaxis procedure as they magnify harmful and counterproductive practices by the toothbrush user.

The tooth and gum brushing procedure has three main focuses: removing plaque and debris from the surfaces of the tooth, protecting and preserving the tooth enamel, and protecting and preserving the gums and gingival margin. This toothbrush and brushing technique brushes and cleans the teeth and gums, while not loosening the gums. Unfortunately, even though prior art electric toothbrushes may be equipped to power scrub debris from the tooth enamel, as the prior art toothbrushes brush across the direction of gum growth and not in the direction of gum growth, they can be damaging to the gingival margin and therefore can be harmful to the gums and teeth.

More specifically, daily home tooth and gum brushing involves bristles, which are an effective, efficient, and affordable system for clearing debris from the tooth enamel before it becomes hardened plaque. However, regardless of the "softness" of the bristle bundles, or the brushing technique and/or angle employed by the tooth brusher (the Bass method, for example), prior art electric toothbrushes inherently brush into the junction of the tooth and the periodontium. The rapidly oscillating and rotating bristle bundles (designed to imitate the professional cup-like buffing tool), the rapidly vibrating bristle bundles, the back-and-forth sweeping bristle bundles, etc. (intended to maximize the rate of bristle-to-tooth scrubbing) unintentionally force bristles into the junction, lift and loosen the gums, and force debris under the gums, all of which are harmful to the gums. This damaging tissue along the gingival margin results in lateral movement of the periodontium away from the tooth cementum-layer upon which it is anchored (a key indication of periodontium disease).

There is, therefore, a need in the art for a toothbrush, and a method for using the same, for achieving proper tooth and gum health and proper brushing and cleaning of the teeth by brushing the teeth in the direction of gum growth from the gum to the tooth crown, and not across or against the direction of gum growth, thereby, among other things, not loosening or lifting the gums. As there is no such toothbrush currently on the market that carries out this method, it is to this need that the present invention is directed. Accordingly, the present invention provides an improved toothbrush, and a method for using the same, that effectively overcomes the aforementioned difficulties and longstanding problems inherent in the art. These problems have been solved in a simple, efficient, and highly effective design for a toothbrush, and preferably an electric toothbrush, and a method for using the same.

BRIEF SUMMARY OF THE INVENTION

Briefly, a preferred embodiment of the present invention is an electric toothbrush for proper brushing of the teeth and gums, including for proper brushing of the teeth and gums so as not to loosen the gums, and a method of using the toothbrush to achieve the goals. One illustrative embodiment of the invention is an electric toothbrush that includes a handle body and an interchangeable stem. Another illustrative embodiment of the invention is an electric toothbrush that includes a unitary handle and stem. In all preferred embodiments, the interchangeable stem includes an elongated neck, a head, a rotating bristle assembly, and a means for rotating the bristle assembly such as a motor. In another illustrative embodiment, the electric toothbrush includes a handle body, an interchangeable stem, and a camera device with intraoral video capability. Preferably, the invention is waterproof or water-resistant.

The stem preferably comprises a rotating bristle assembly mounted on an elongate neck, a bristle guard that acts as a mouth or cheek shield for covering a portion of the rotating bristle assembly, a means for mounting the bristle assembly to the stem (in the interchangeable stem embodiment), a means for rotating the bristle assembly, a means for mounting the stem to the handle body, and a means for connecting the bristle assembly to a motor for rotating the bristle assembly.

The elongate neck has a first end opposite a second end. In the interchangeable stem embodiment, the first end of the elongate neck is configured to detachably engage with the handle body, and comprises the means for mounting the stem to the handle body. In the non-interchangeable stem embodiment, the first end of the elongate neck is directly attached to, or a structural extension of, the handle body. The second end of the elongate neck is terminated by the head, and comprises the rotating bristle assembly and the bristle guard.

The head comprises a bristle assembly that can rotate (sometimes referred to as a rotating bristle assembly herein) and is longitudinally aligned with the longitudinal axis of the interchangeable stem. The rotating bristle assembly has a first end opposite a second end. The first end of the rotating bristle assembly is proximal to the second end of the elongate neck. The bristle guard extends from the second end of the neck around the back side of the rotating bristle assembly. Extending from the second end of the cylindrical bristle body is the means for rotating the bristle assembly, such as, for example, a metal or plastic rod or wire, extending through the elongate neck towards the handle body. The means for rotating the bristle assembly cooperates with the motor for rotating the bristle assembly when the motor is activated.

The bristle guard is attached to or part of the stem proximal to the first end of the elongate neck and proximal to the bristle assembly, and extends circumferentially around and laterally spaced apart from the rotating bristle assembly. The bristle guard describes an arc segment along the bristle assembly. The longitudinal axis of the bristle guard is parallel to the longitudinal axis of the interchangeable stem. The bristle guard acts to prevent the bristle assembly from contacting the inner cheek of the user when the device is being operated.

The handle body preferably comprises a cylindrical portion having a hollow interior within which the motor and the power source, and appurtenant wiring and electrical connectivity and operating means, are located. The handle body further comprises a means for mounting the stem to the bristle assembly (in the interchangeable stem embodiment), a means for accessing the interior of the handle body so as to be able to change out batteries for powering the motor (in an embodiment comprising exchangeable batteries), and a switch means for activating and deactivating (turning on and off) the motor. Preferably, the motor is configured such that the rotating bristle assembly can rotate in both directions, such as clockwise and counterclockwise, as the user desires.

The handle body further may comprises a means for detachably engaging or rigidly or permanently engaging a camera device to an exterior side of the cylindrical potion such that intraoral video may be obtained during operation of the electric toothbrush. Moreover, the camera device preferably is configured for 640×480 resolution or upwards of 4K HD video or any other video capture capability known to a person having ordinary skill in the art. The camera device may be an optical device consisting of a rigid or flexible tube, and/or cylindrical optical or optically conductive cable, and/or any communications pathway, with a lens on one end, and a camera sensor on the other end linked together by a relay optical system there between. The camera device, when detachably engaged to the handle body, or when permanently and rigidly attached to the handle body, may aim its aperture towards the oral cavity of a user of the electric toothbrush so as to capture intraoral video. The intraoral video may then be transmitted and/or processed for useful display to the user of the electric toothbrush, such as to a smart phone device or other video display.

The means for rotating the bristle assembly is operably connectable to the motor or to an extension of the motor, whereby when the motor is activated, the motor turns the means for rotating the bristle assembly, thus rotating the bristle assembly. The motor preferably can rotate the bristle assembly in both directions; therefore, the device further comprises a switch that can cause the motor to rotate in both directions. Alternatively, the device can comprise appropriate gearing so as to accomplish the same result of allowing the rotating bristle assembly to rotate in both directions. Thus, when the means for rotating the bristle assembly is powered, the rotating bristle assembly is selectably motorized to rotate clockwise or counterclockwise via mechanical electrical engagement with the means for rotating the bristle assembly.

In another illustrative embodiment, the bristle guard of the interchangeable stem comprises a concave bristle-facing side and a convex non-bristle facing side. The non-bristle facing side can define or comprise a raised surface texture or raised surface feature that is abrasive or frictional and that can be used for tongue, cheek, and gum cleaning and/or massaging.

A preferred embodiment of the method for using the toothbrush comprises activating the means for rotating the bristle assembly (the motor) such that the rotating bristle assembly is spinning in a first direction and applying the rotating bristle assembly to a first set of the user's teeth and gums such that the bristles rotating in the first direction rotate in a direction from the user's gums towards crowns of the user's teeth. In this method, the rotating bristles rotate in the direction of gum growth, namely from the gums towards the crown of the teeth, thereby not lifting or loosening the gums from the teeth, not brushing across or against the direction of gum growth, and not forcing debris up under the gums and between the gums and the teeth.

The toothbrush preferably is structured to allow the bristles to rotate in a second direction opposite the first direction so that the toothbrush can be used on all of the user's teeth and still achieve the goal of having the bristles rotate in a direction from the user's gums towards the crowns of the user's teeth. Thus, the user also can activate the means for rotating the bristle assembly such that the rotating bristle assembly is spinning in a second direction and applying the rotating bristle assembly to a second set of the user's teeth and gums such that the bristles rotating in the second direction also rotate in a direction from the user's gums towards crowns of the user's teeth. As above, the rotating bristles also rotate in the direction of gum growth, namely from the gums towards the crown of the teeth, thereby not lifting or loosening the gums from the teeth, not brushing across or against the direction of gum growth, and not forcing debris up under the gums and between the gums and the teeth.

Thus, the electric toothbrush and the method for using the electric toothbrush is configured to effectively and efficiently remove plaque and debris from the user's teeth while protecting and preserving a user's gums, gingival margin and periodontium by recreating a proper dental tooth and gum brushing procedure and preventing a loosening of a user's gums, thus increasing the overall health of a user's gums and oral cavity.

These features, and other features and advantages of the present invention will become more apparent to those of ordinary skill in the relevant art when the following detailed description of the preferred embodiments is read in conjunction with the appended drawings in which like reference numerals represent like components throughout the several views.

DETAILED DESCRIPTION OF PREFERRED EMBODIMENTS

Figure 1A:
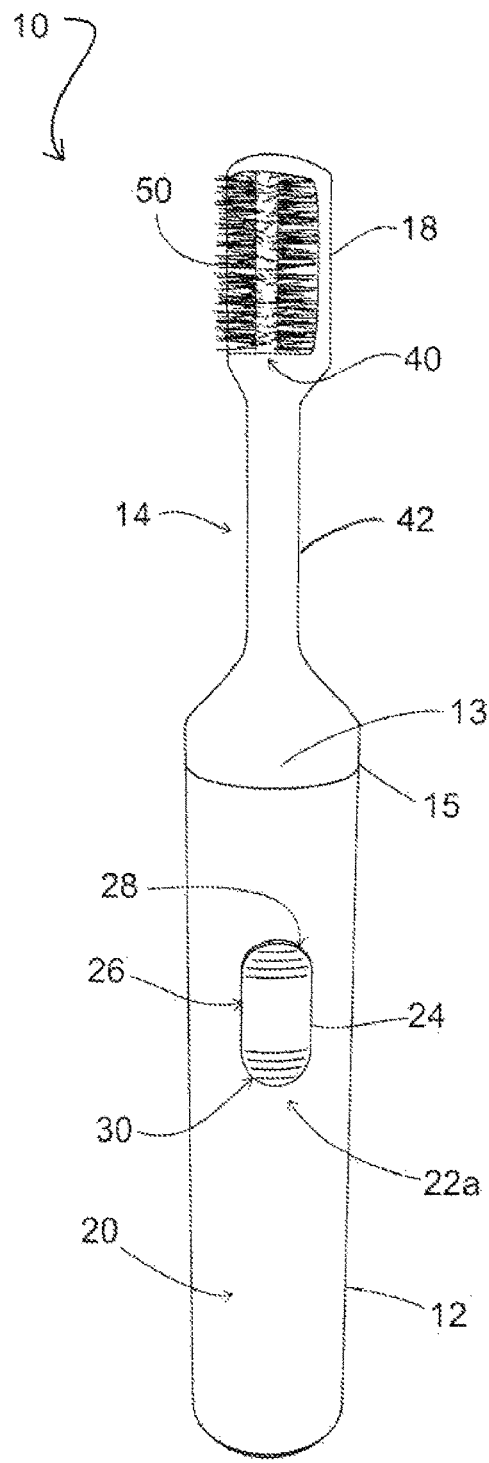
FIG. 1A is a front side perspective view of an embodiment of an electric toothbrush of the present invention.

Preferred embodiments and aspects of the present disclosure provide an electric toothbrush for proper brushing of the teeth and gums so as not to cause a lifting or loosening of the gums, and a method of using the toothbrush to achieve these ends. Unlike prior art electric toothbrushes, the toothbrush of the present disclosure is configured to effectively and efficiently remove debris from the tooth enamel, to protect and preserve the gingival margin, and to maintain healthy gums by not adversely acting on the gums during the brushing procedure. The toothbrush creates a proper tooth and gum brushing procedure at home on a daily basis, while at the same time brushing the teeth and gums in a manner that prevents the lifting and loosening of the gums from the teeth. Moreover, embodiments of the electric toothbrush may be outfitted with an intraoral video camera device.

More specifically, by a simple flip of a switch, and regardless of the specific tooth or teeth and gums being brushed, the electric toothbrush is configured to brush along the gingival margin in a direction from the gums towards the tooth crown. The toothbrush, thereby, prevents the bristles from being forced improperly against or into the junction of the tooth and the periodontium and, as a result, prevents the lifting and/or loosening of the gums from the teeth. As such, the toothbrush clears debris away from the tooth enamel (before it becomes hardened plague) without sacrificing the gingival margin and without adversely affecting the gums.

The toothbrush, and the method for using the same, facilitates appropriate daily prophylaxis by steering the tooth brusher away from harmful behavior, and by affording the very young, the elderly, the infirm, and the lazy with an affordable tool that requires not only one hand, but minimal hand, wrist, and arm motion to operate. Moreover, embodiments of the toothbrush can have a bristle shield that extends around the bristle structure of the toothbrush. The bristle shield is configured to shield the bristles from over-the-air contamination, when it is in a "full" bathroom environment, and to facilitate US American Dental Association (ADA)-recommended drying of the bristles between brushings.

Furthermore, embodiments of the electric toothbrush may comprise a camera device with intraoral video capability, as well as a power source, wiring, electronic boards and circuitry, system bus, and/or means for transmitting video data for use, directly or indirectly, by a user. In this way, the electric toothbrush may be further configured to facilitate appropriate daily brushing of the teeth and gums as the intraoral video capability allows the user to see and target brushing along the gingival margin, and recognize areas with high debris quantity requiring additional attention. As the appropriate daily brushing of the teeth and gums accomplished by the electric toothbrush of the present invention requires minimal toothpaste (and the foam created therefrom), a video capable embodiment is not limited by obstructed video imaging. This would be the outcome of merely sticking a video camera on the side of a traditional prior art toothbrush that encourages harmful brushing of the teeth and gums.

Embodiments of the toothbrush comprise an interchangeable stem and an attachment means for allowing the attachment of the interchangeable stem to a handle body. The interchangeable stem includes, at one end, a toothbrush head with a rotating bristle assembly and a neck for attachment via the attachment means to the handle body. The rotation means utilized to allow the rotation of the interchangeable stem may be a component of the stem or the handle body depending on the embodiment. It is, however, preferred that the rotation means be a part of the handle body in order to reduce the manufacturing costs of the interchangeable stems. This also allows for the stems to be marketed relatively inexpensively and independently of the handle body.

Figure 1B:
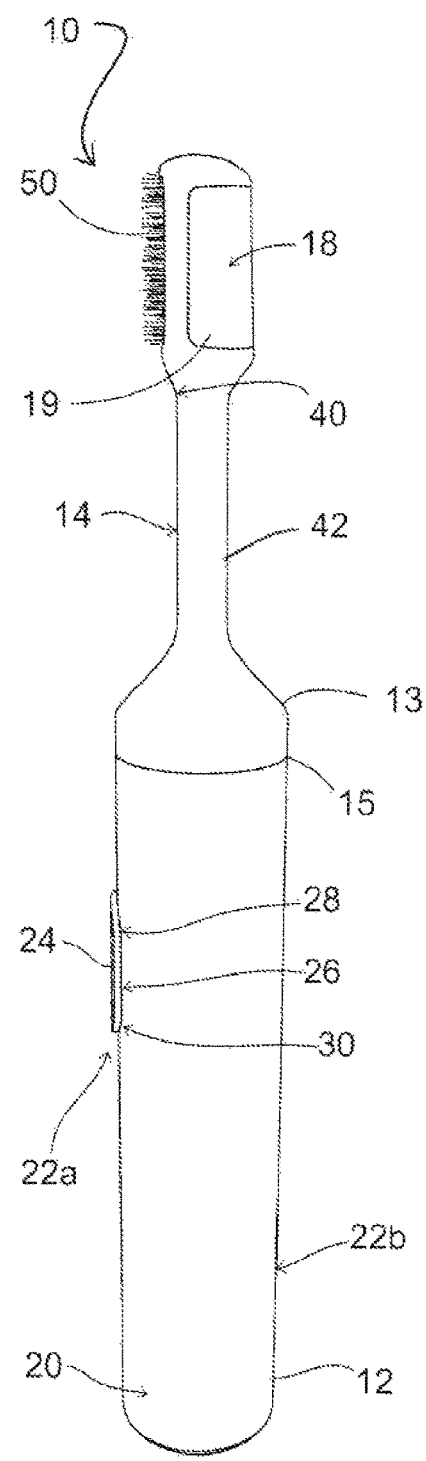
FIG. 1B is a right side perspective view of the toothbrush of FIG. 1A turned 90 degrees.
Figure 1C:
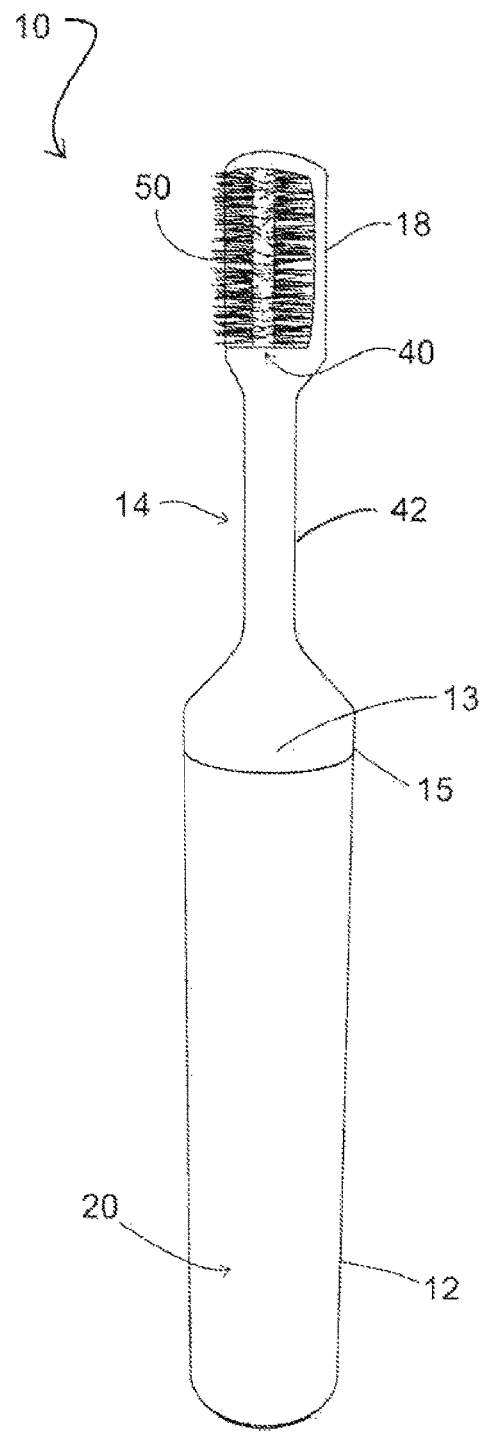
FIG. 1C is front view of a push-button waterproof switch suitable for use with the present invention.
Figure 1D:
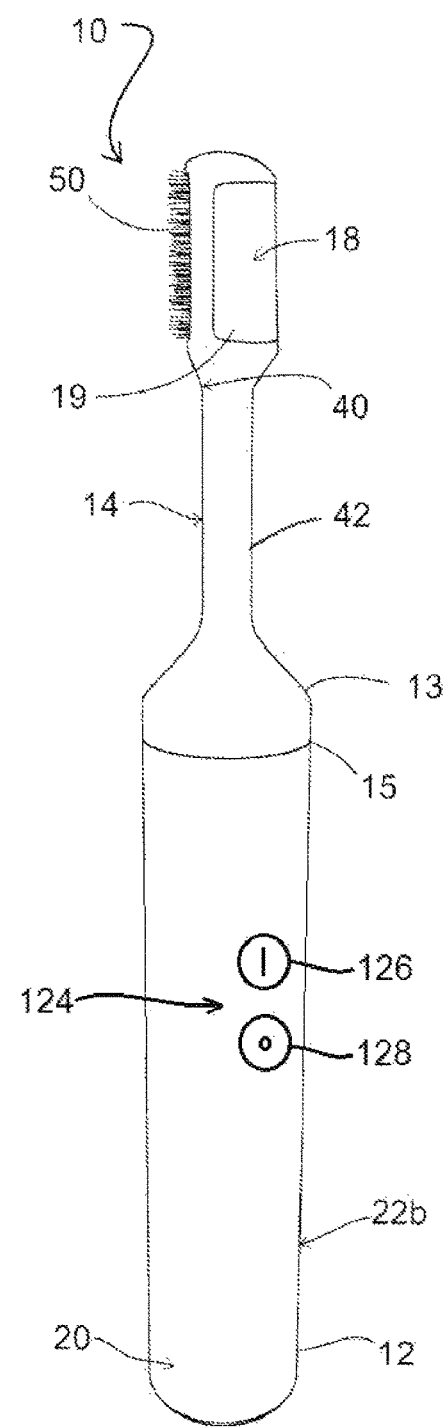
FIG. 1D is front view of a push-button waterproof switch suitable for use with the present invention.
Figure 2A:
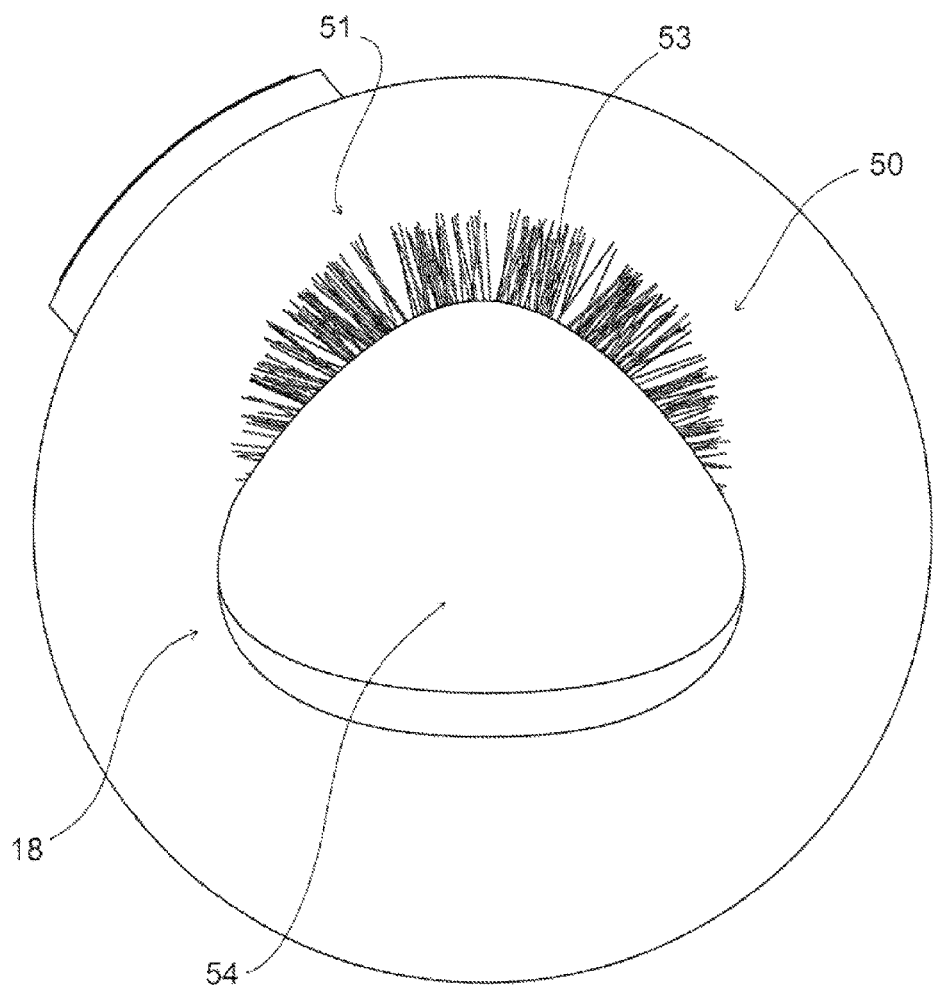
FIG. 2A is a top view of the toothbrush of FIG. 1A.
Figure 2B:
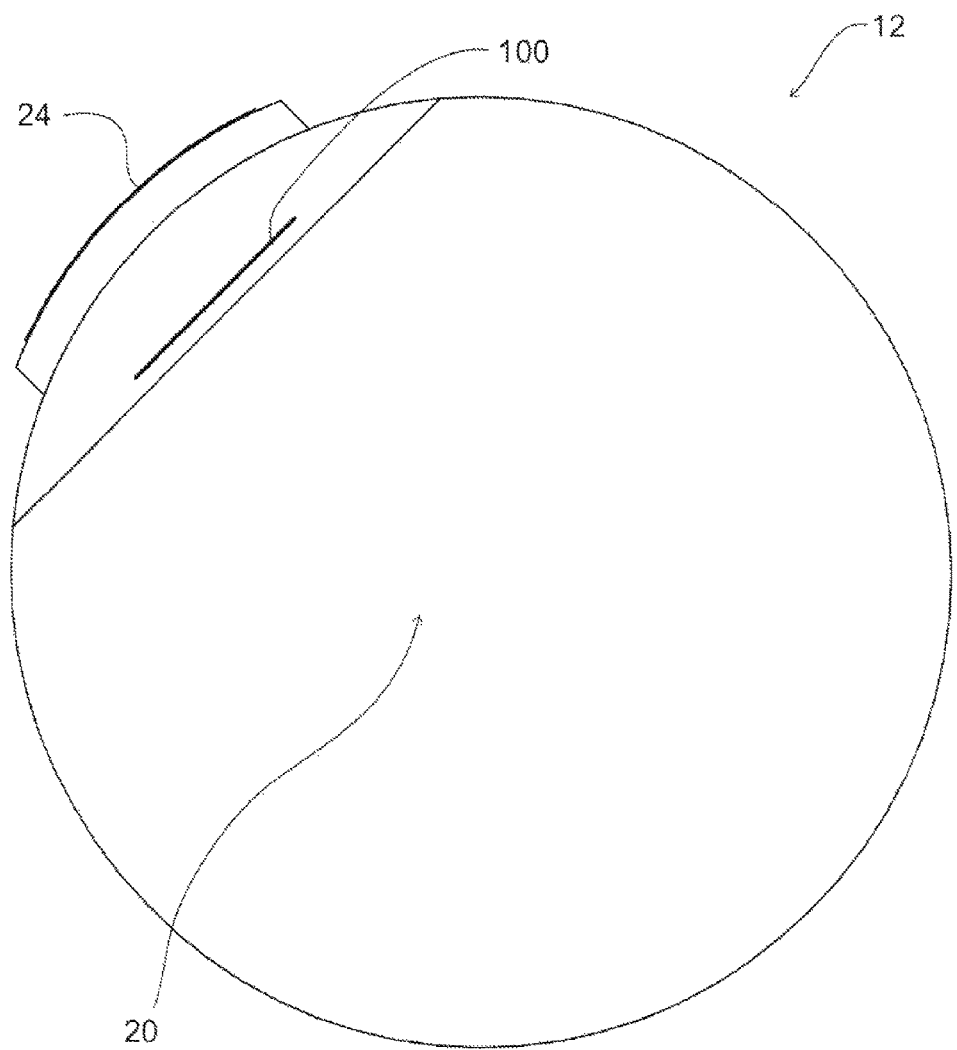
FIG. 2B is a bottom view of the toothbrush of FIG. 1A.

Referring now to the drawings, wherein the showings are for purposes of illustrating the various embodiments of the present disclosure only, and not for purposes of limiting the same, FIGS. 1A-1D and 2A-2B show the general features of the present invention. FIG. 1A is a front side perspective view of an embodiment of an electric toothbrush of the present invention, FIG. 1B is a right side perspective view of the toothbrush of FIG. 1A turned 90 degrees, FIG. 1C is front view of a push-button waterproof switch suitable for use with the present invention, and FIG. 1D is front view of a push-button waterproof switch suitable for use with the present invention. FIG. 2A is a top view of the toothbrush of FIG. 1A, and FIG. 2B is a bottom view of the toothbrush of FIG. 1A.

Figure 3:
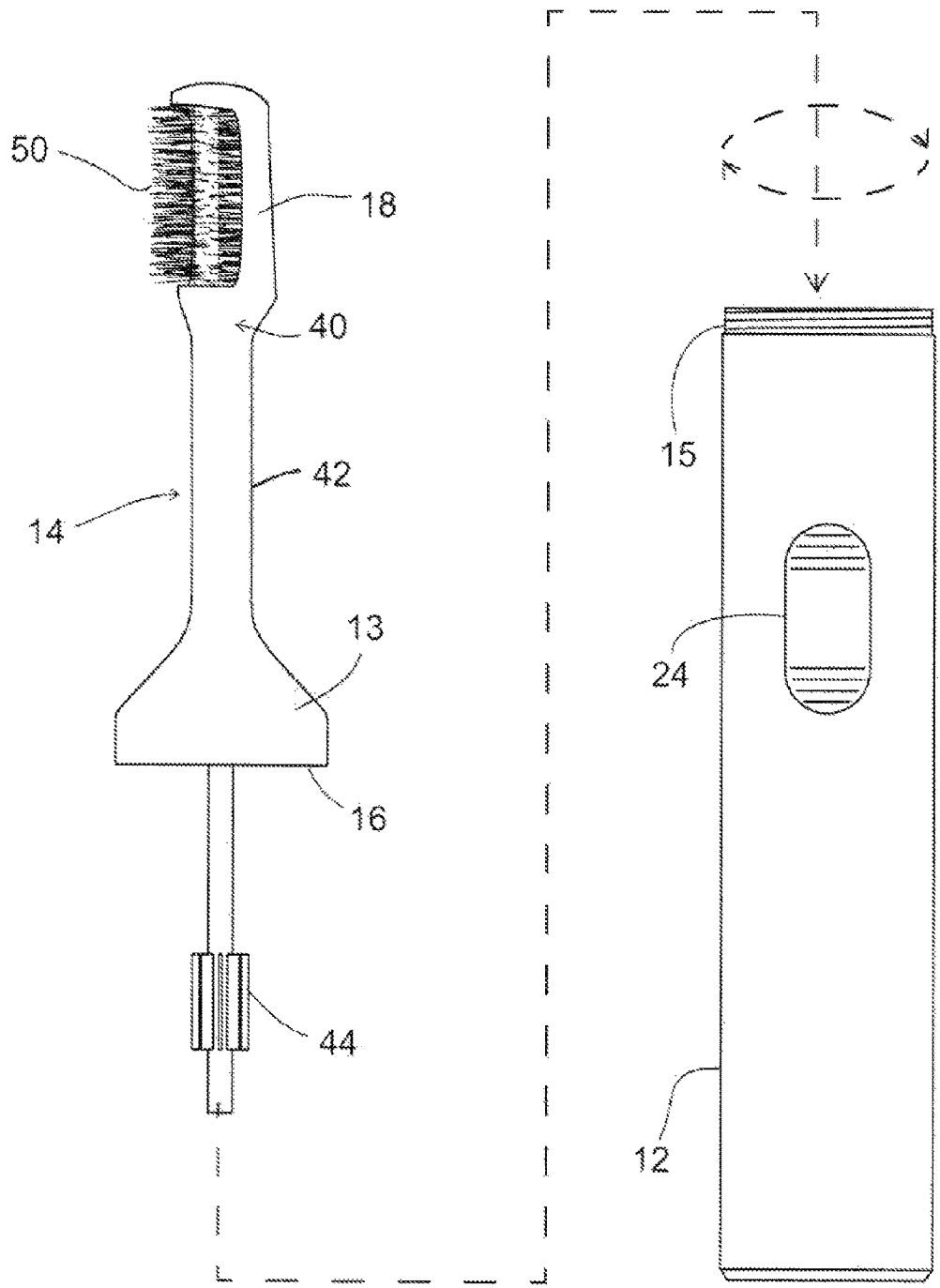
FIG. 3 is a partially exploded perspective view of the toothbrush of FIG. 1 illustrating how an interchangeable stem and a handle body detach and attach to one another.
Figure 4A:
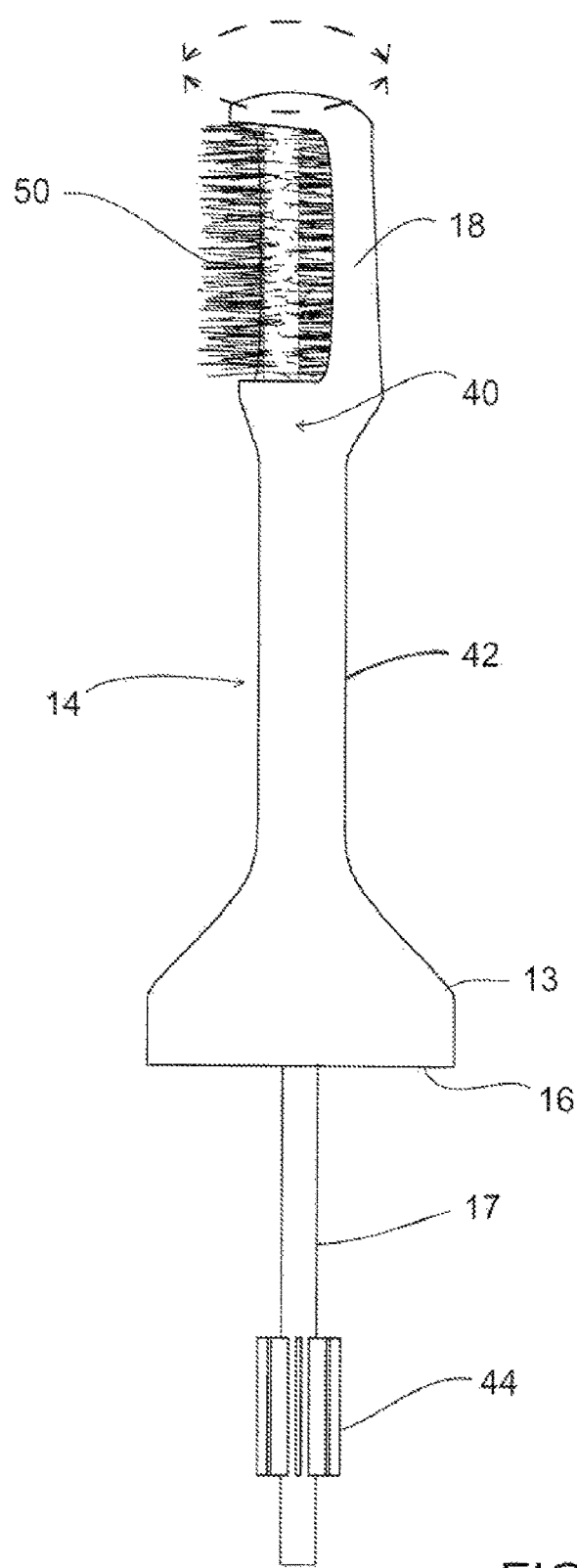
FIG. 4A is an enlarged front perspective view of the interchangeable stem of FIG. 3.
Figure 4B:
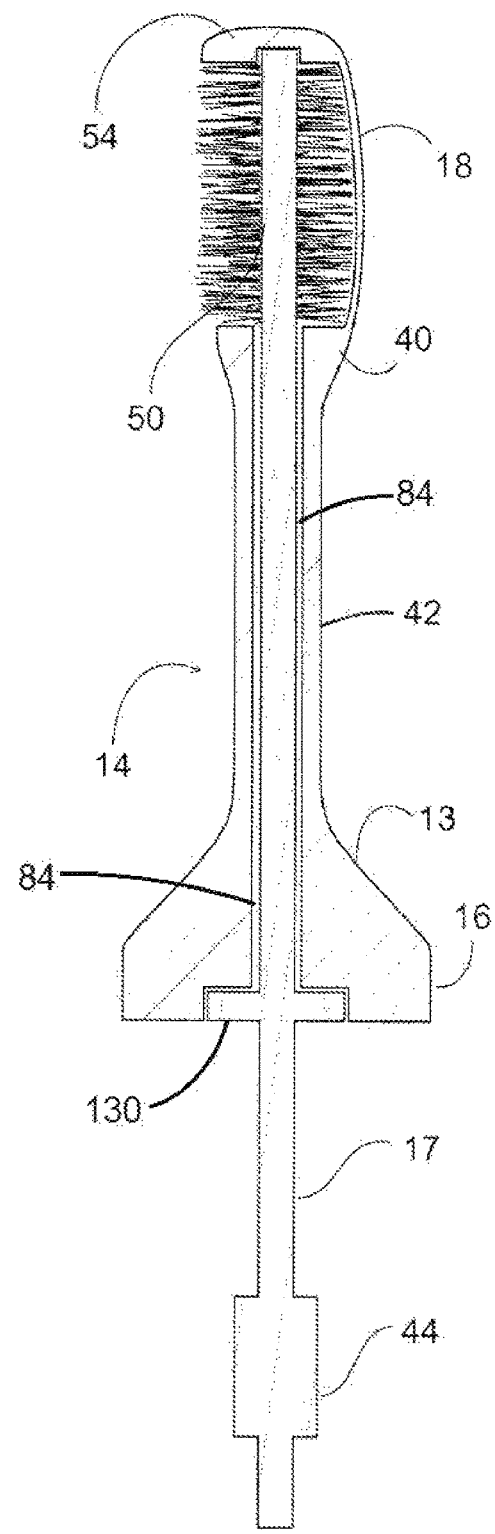
FIG. 4B is a cross section of the interchangeable stem of FIG. 4A
Figure 5:
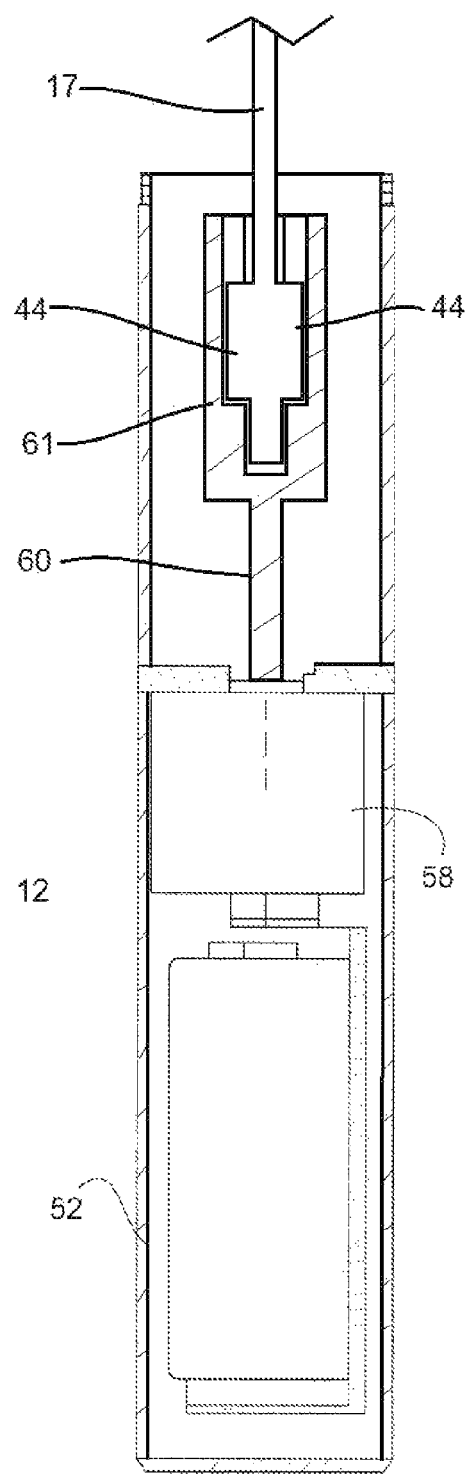
FIG. 5 is a cross-sectional view of an illustrative schematic of the handle body of FIG. 3.

FIGS. 3, 4A-4B, and 5 show the additional general features of an interchangeable stem embodiment of the invention. FIG. 3 is a partially exploded perspective view of the toothbrush of FIG. 1 illustrating how an interchangeable stem and a handle body detach and attach to one another. FIG. 4A is an enlarged front perspective view of the interchangeable stem of FIG. 3. FIG. 4B is a cross section of the interchangeable stem of FIG. 4A. FIG. 5 is a cross-sectional view of an illustrative schematic of the handle body of FIG. 3.

Figure 6:
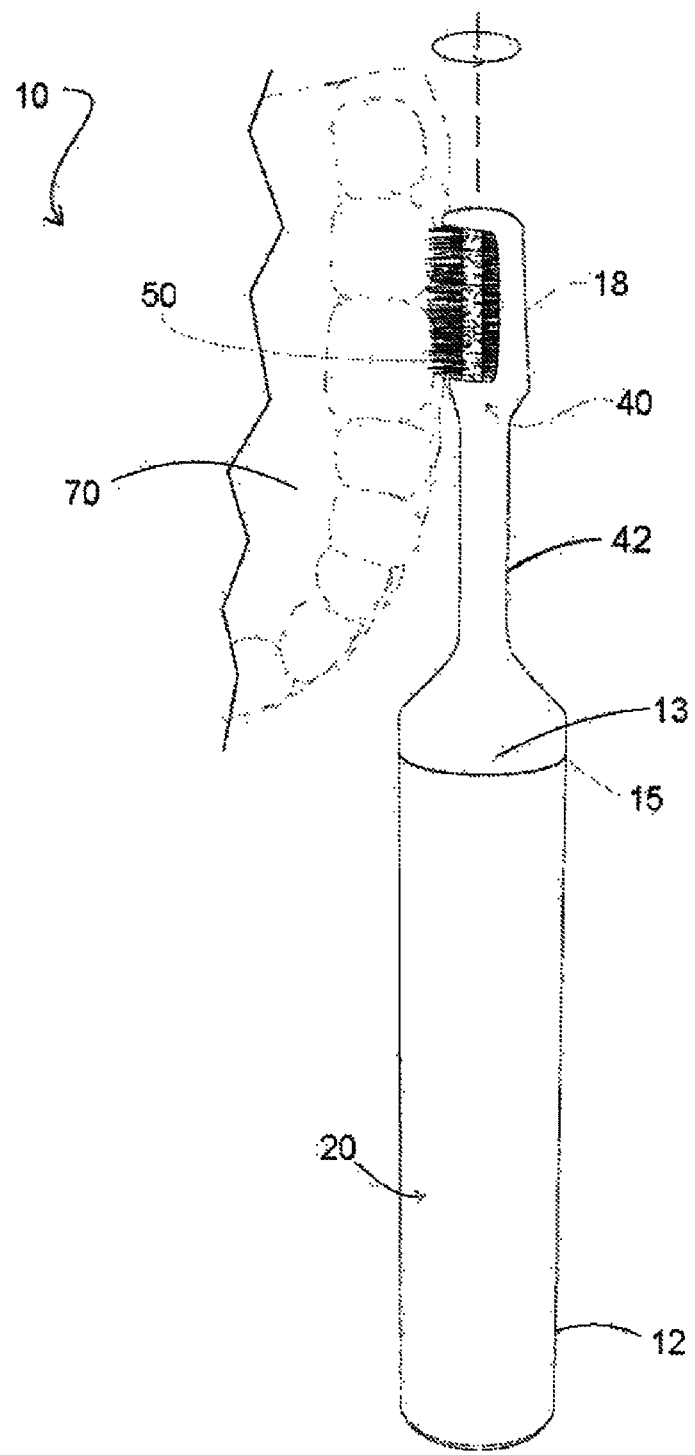
FIG. 6 is a perspective view of the toothbrush of FIG. 1 operating on the outside facing surfaces of teeth on the upper right side, or the lower left side, of a user's jaw, illustrating a method according to the invention.
Figure 7:
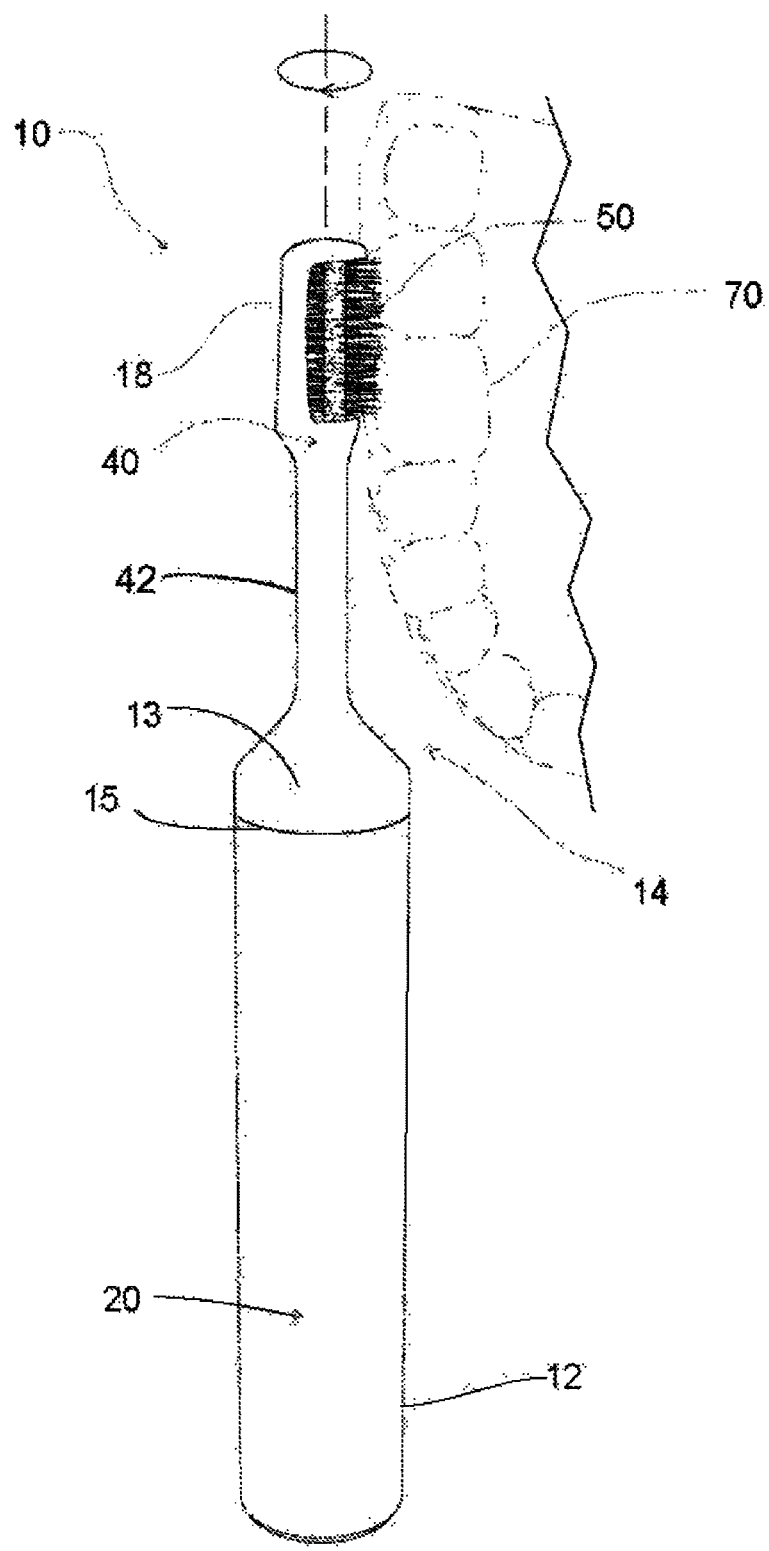
FIG. 7 is a perspective view of the toothbrush of FIG. 1 operating on the outside facing surfaces of teeth on the upper left side, or the lower right side, of a user's jaw, illustrating a method according to the invention.
Figure 8:
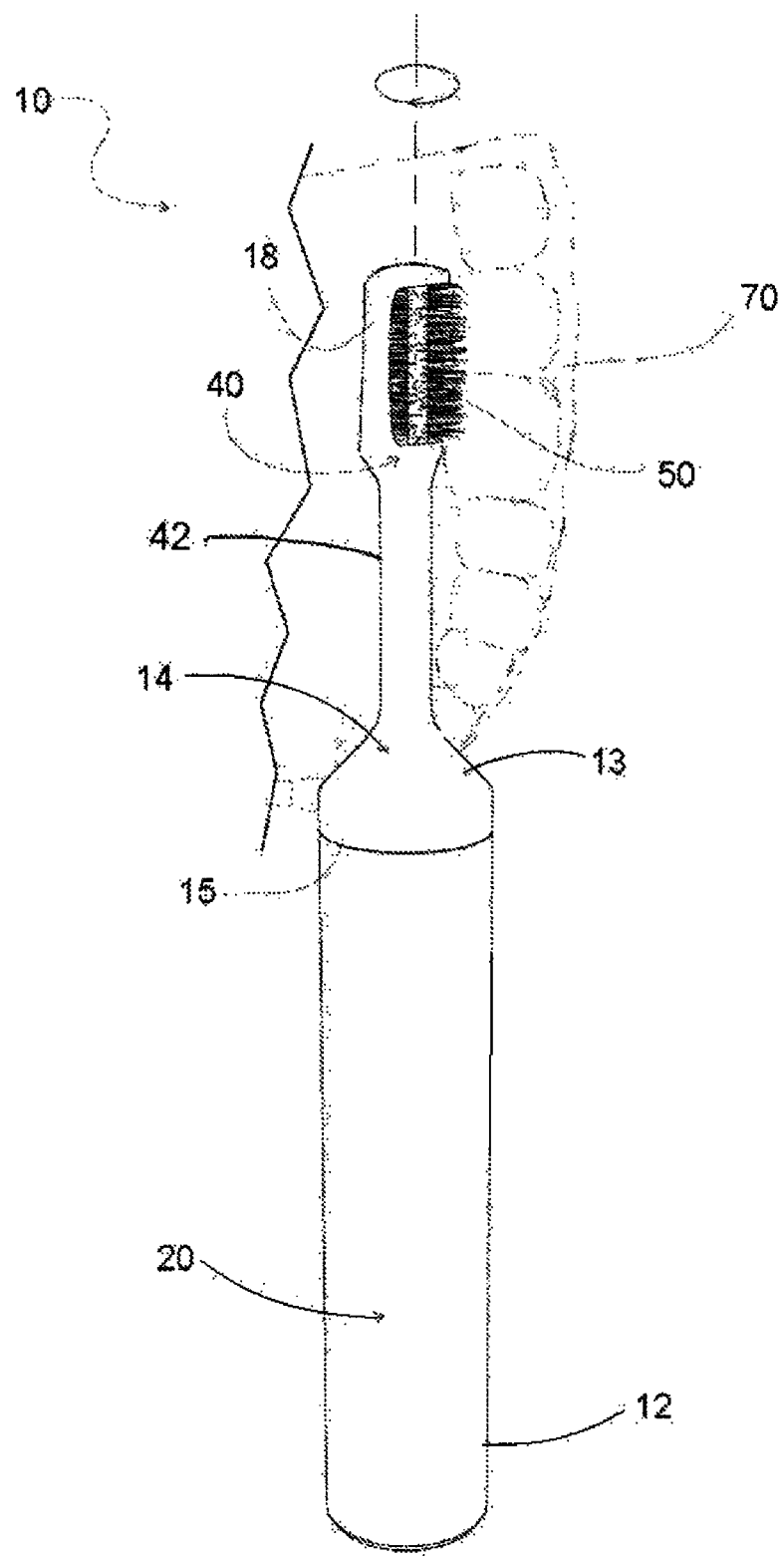
FIG. 8 is a perspective view of the toothbrush of FIG. 1 operating on the inside facing surfaces of teeth on the upper right side, or the lower left side, of a user's jaw, illustrating a method according to the invention.
Figure 9:
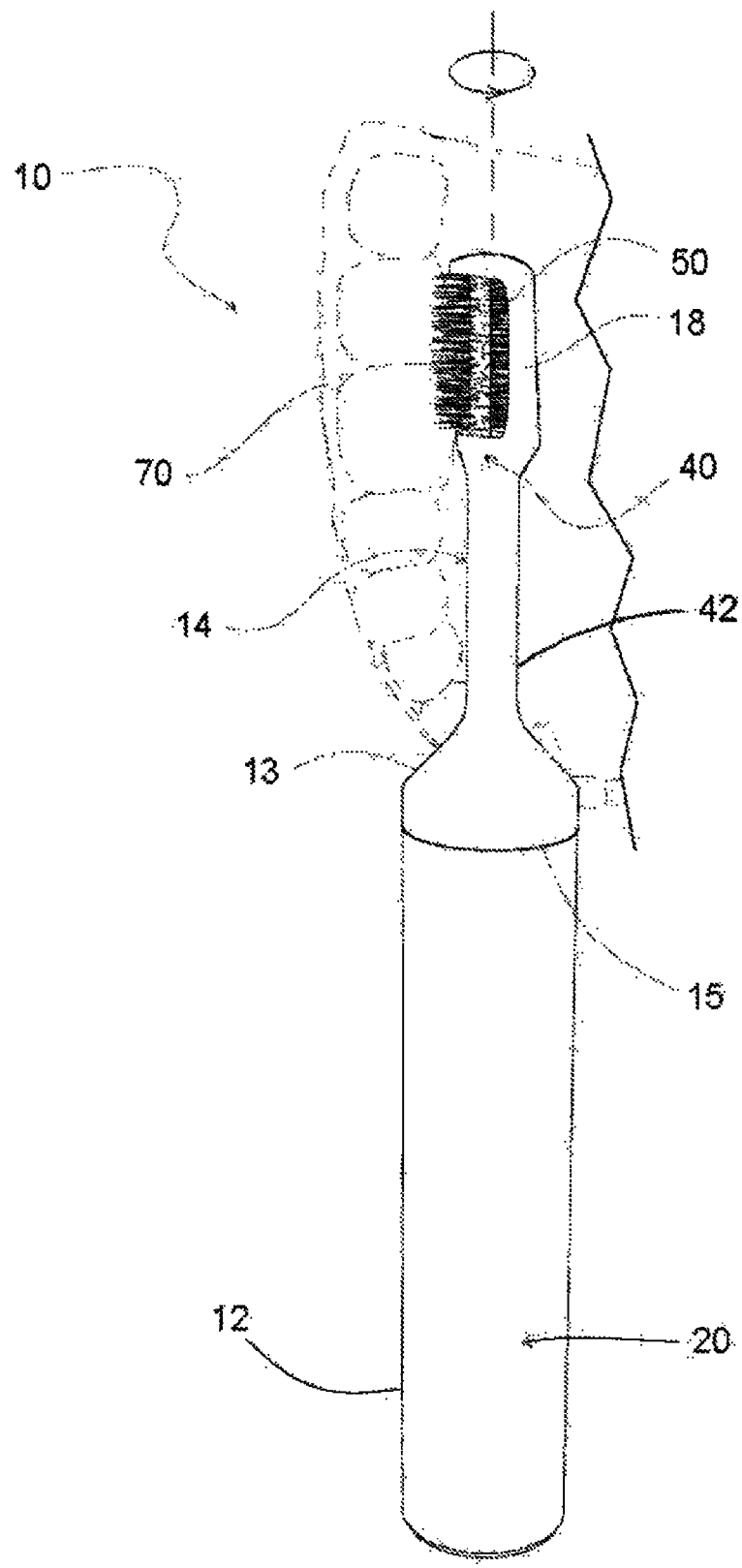
FIG. 9 is a perspective view of the toothbrush of FIG. 1 operating on the inside facing surfaces of teeth on the upper left side, or the lower right side, of a user's jaw, illustrating a method according to the invention.

FIGS. 6-9 show an embodiment of an electric toothbrush of the present invention in use, illustrate a preferred method for using the toothbrush of the present invention, and illustrate a preferred method of brushing a user's teeth according to the invention. FIG. 6 is a perspective view of the toothbrush of FIG. 1 operating on the outside facing surfaces of teeth on the upper right side, or the lower left side, of a user's jaw. FIG. 7 is a perspective view of the toothbrush of FIG. 1 operating on the outside facing surfaces of teeth on the upper left side, or the lower right side, of a user's jaw. FIG. 8 is a perspective view of the toothbrush of FIG. 1 operating on the inside facing surfaces of teeth on the upper right side, or the lower left side, of a user's jaw. FIG. 9 is a perspective view of the toothbrush of FIG. 1 operating on the inside facing surfaces of teeth on the upper left side, or the lower right side, of a user's jaw.

Figure 10A:
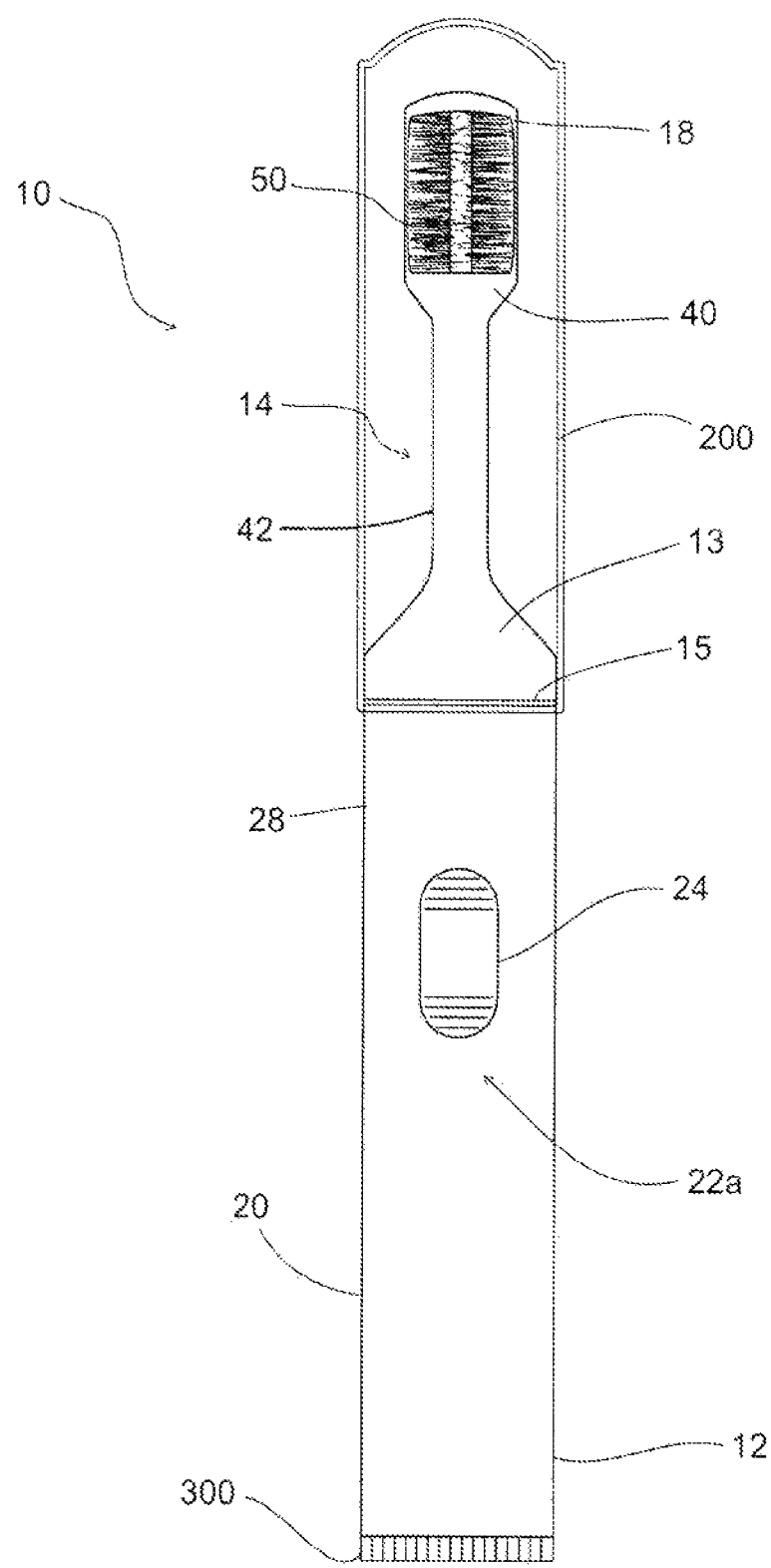
FIG. 10A is a front side perspective view of an electric toothbrush of the present invention including a second embodiment of the handle and a second embodiment of the bristle shield and an activator slide switch.
Figure 10B:
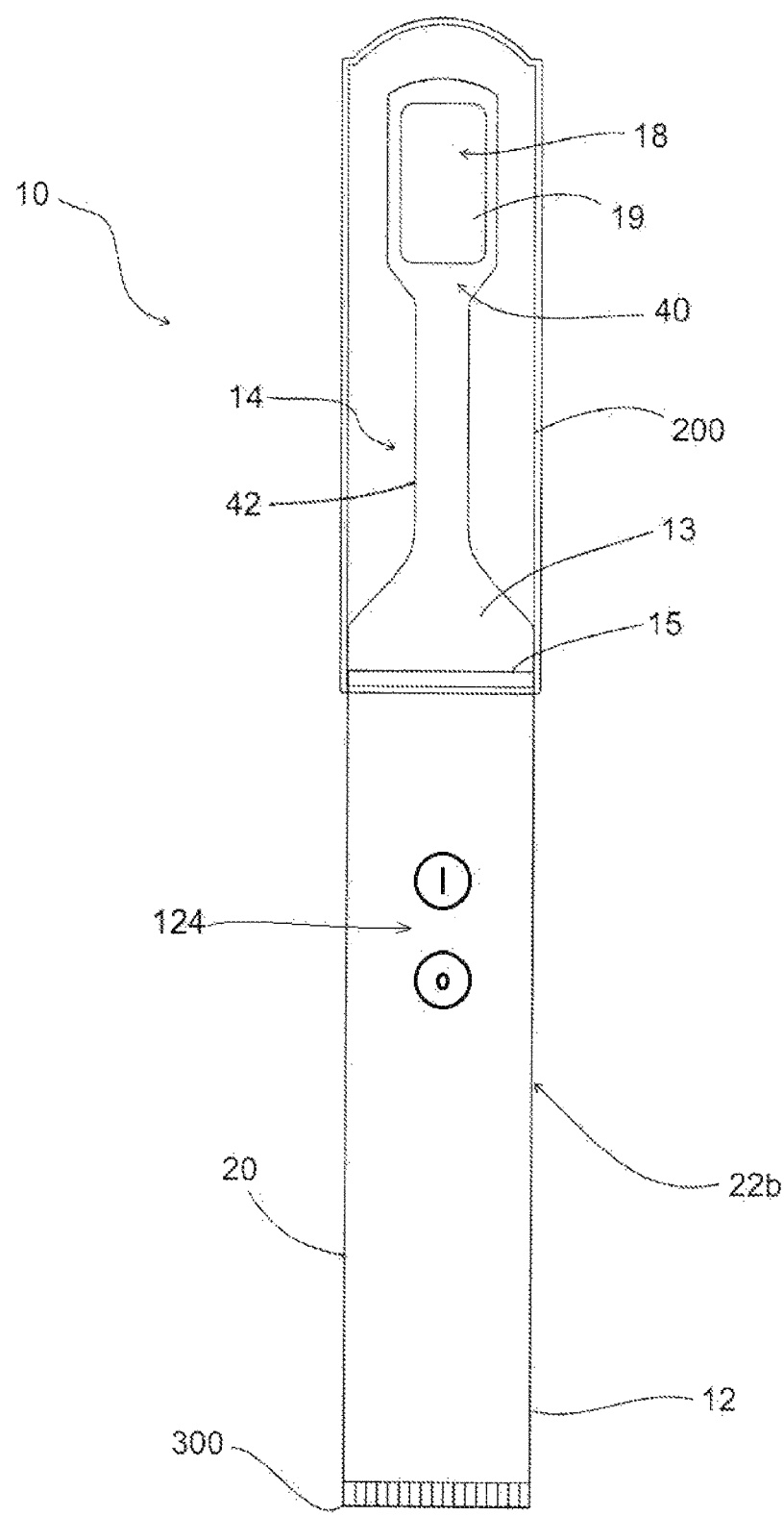
FIG. 10B is a rear side perspective view of the toothbrush of FIG. 10A with a push button switch.

FIG. 10A is a front side perspective view of an electric toothbrush of the present invention including a second embodiment of the handle and a second embodiment of the bristle shield with an activator switch. FIG. 10B is a rear side perspective view of the toothbrush of FIG. 10A with a push button switch.

Figure 11A:
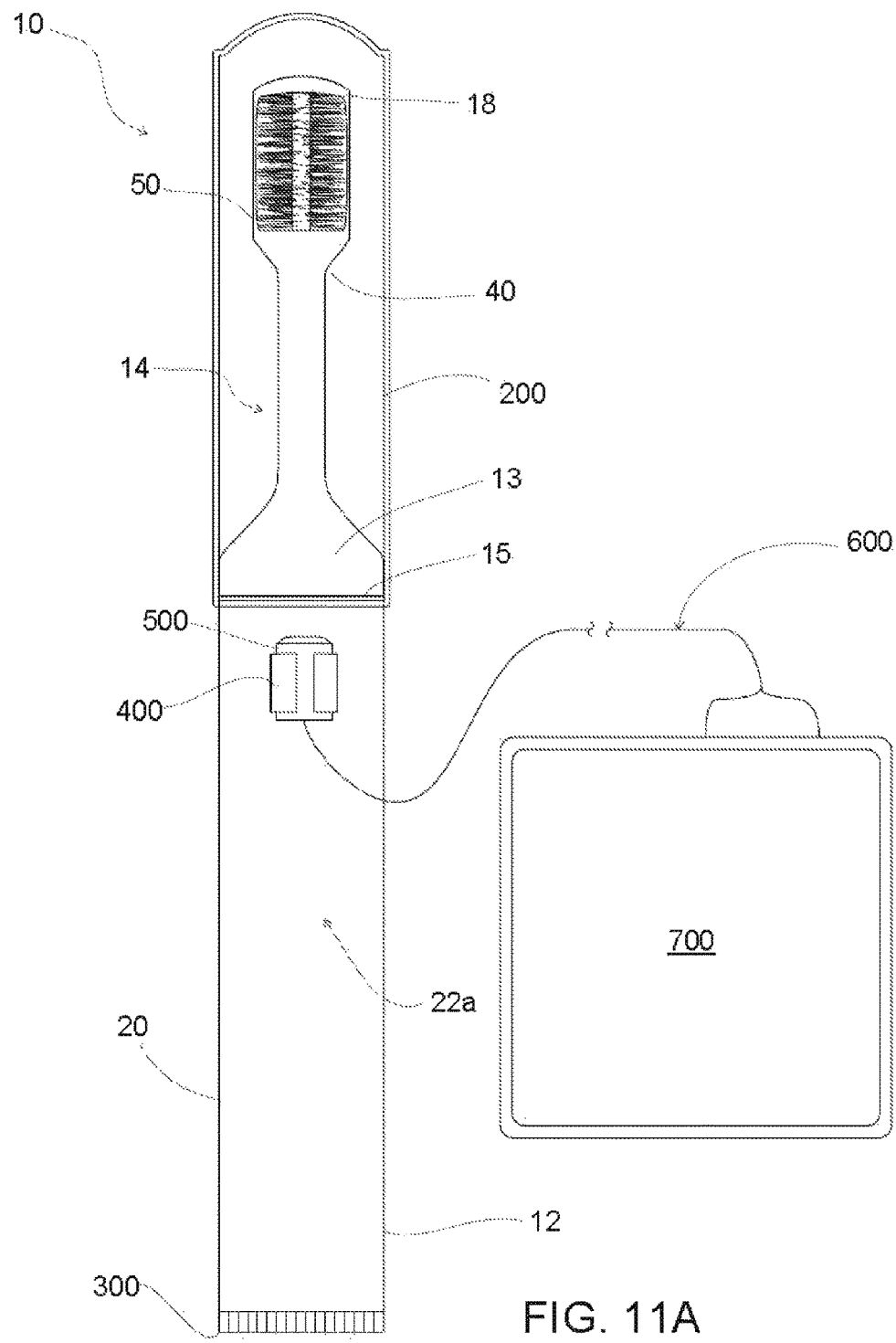
FIG. 11A is a front side perspective view of a first embodiment of a video capable electric toothbrush of the present invention.
Figure 11B:
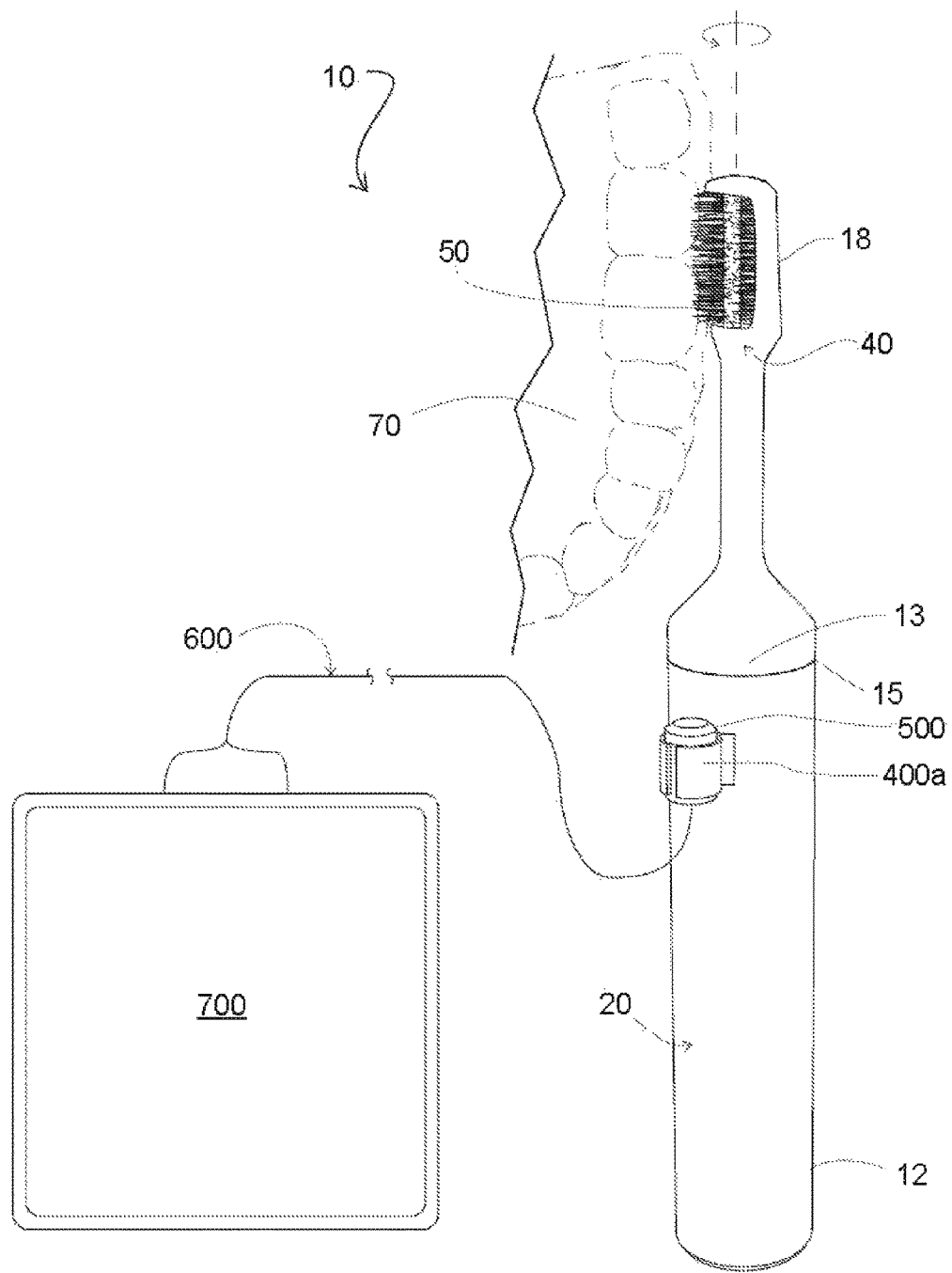
FIG. 11B is a perspective view of the electric toothbrush of FIG. 11A operating on the outside facing surfaces of teeth and gums on the upper right side, or the lower left side, of a user's jaw.
Figure 11C:
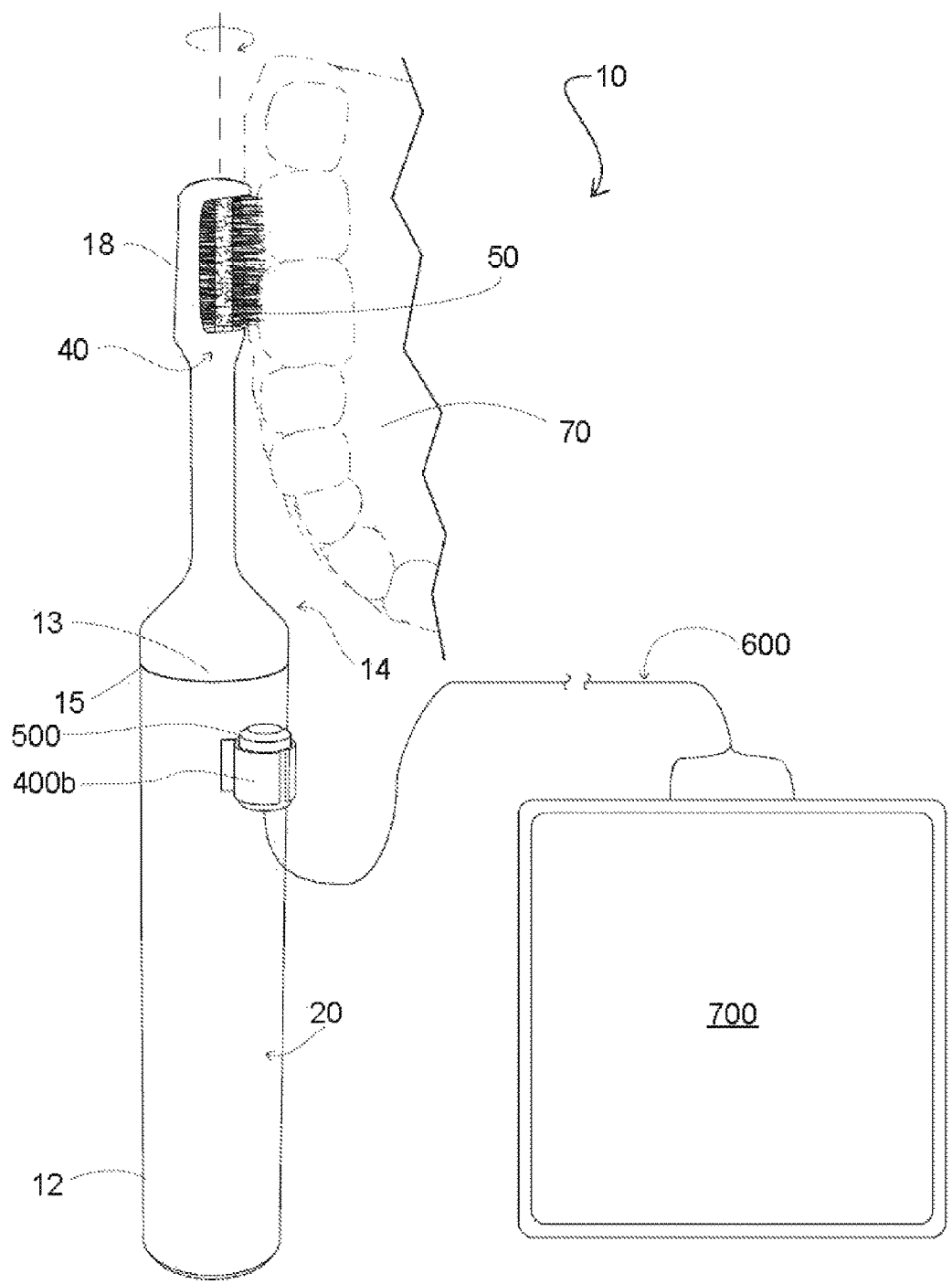
FIG. 11C is a perspective view of the electric toothbrush of FIG. 11A operating on the outside facing surfaces of teeth and gums on the upper left side, or the lower right side, of a user's jaw.
Figure 12:
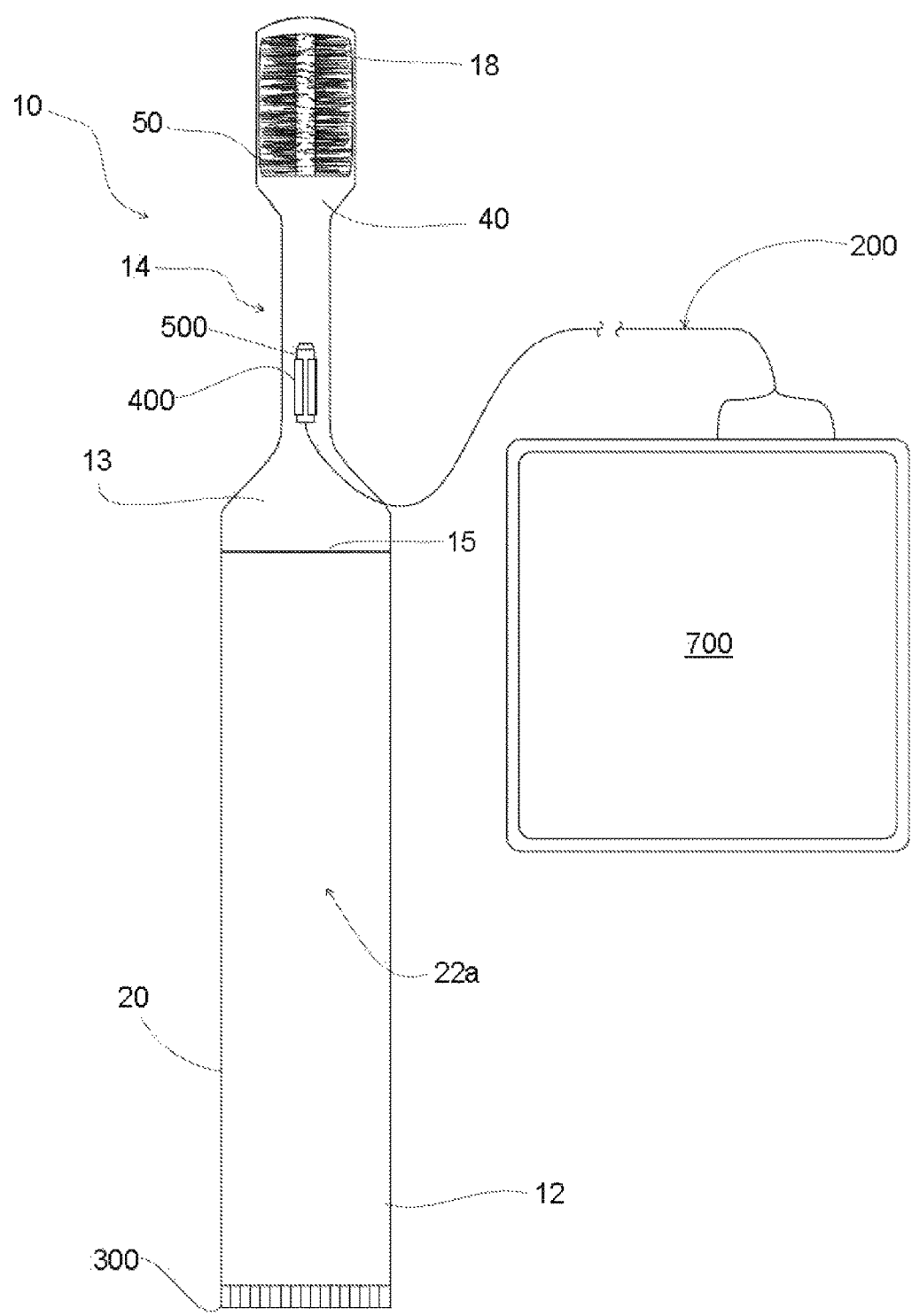
FIG. 12 is a front side perspective view of a second embodiment of a video capable electric toothbrush of the present invention.

FIG. 11A is a front side perspective view of a first embodiment of a video capable electric toothbrush of the present invention, with the camera device located on the handle body. FIG. 11B is a perspective view of the electric toothbrush of FIG. 11A operating on the outside facing surfaces of teeth and gums on the upper right side, or the lower left side, of a user's jaw. FIG. 11C is a perspective view of the electric toothbrush of FIG. 11A operating on the outside facing surfaces of teeth and gums on the upper left side, or the lower right side, of a user's jaw. FIG. 12 is a front side perspective view of a second embodiment of a video capable electric toothbrush of the present invention with the camera device located on the stem.

Referring now to FIGS. 1A-1D, 2A-2B, 3, and 4A-4C, one embodiment of the toothbrush 10 comprises a handle body 12 (also referred to as just the handle body 12) and an interchangeable stem 14 (also referred to as just the stem 14) having a head 40 with a rotating bristle assembly 50 (also referred to as the bristle assembly) comprising bristles 53. The handle body 12 comprises the motor 58, battery 56, and electrical components for powering the bristle assembly 50, and for providing a suitable handgrip. The interchangeable stem 14 comprises the bristle assembly 50 for brushing the teeth and gums.

Another embodiment of the toothbrush 10 is a unitary device in which the stem 14 is attached, permanently, to the handle body 12. Also in this embodiment, the handle body 12 comprises the motor 58, battery 56, and electrical components for powering the rotating bristle assembly 50, and for providing a suitable handgrip, and the stem 14 comprises the rotating bristle assembly 50 for brushing the teeth.

The handle body 12 comprises an ergonomic outer surface 20, and an internal cavity 52 for containing a rotation means. The rotation means comprises a battery 56, a motor 58, and a set of electrical and transmission components. The handle body 12 may have a larger diameter than a standard, prior art electric toothbrush, which makes the handle body 12 more comfortable and easier to use as less force is required to stably hold the toothbrush 10. Also, when the handle body 12 is larger, the toothbrush 10 requires less rotational turning about its longitudinal axis than is required by a smaller diameter handle.

Furthermore, the handle body 12 is preferably generally cylindrical in shape and has a cross section that is predominantly circular, preferably between about one-half inch to one and one-half inches in diameter, and more preferably approximately one inch in diameter. Handle body 12 further may comprise a generally flat portion 22 defined by a chord of the circular cross section of the handle body 12. Along the surface of the flat portion 22, the handle body 12 comprises an activator slide 24 (a switch) configured to turn the toothbrush 10 "on" and "off" and to control the rotational direction (clockwise or counterclockwise) of the rotating bristle assembly 50 during operation. Therefore, the handle body 12 may be oversized with the front flat surface 22 to enhance manual dexterity, and to make gripping more comfortable for the user. Alternatively, the handle body 12 may be completely cylindrical, or have an oval or other geometric cross section, and the activator slide 24 may be simply mounted on or through the wall of the handle body 12.

Activator slide 24 preferably slides within a channel 26. When the activator slide 24 is in a first position (i.e., when activator slide 24 is fully slid towards a first end 28 of the channel 26), the electric toothbrush 10 is in a first "on" position and the cylindrical rotating bristle assembly 50 rotates in a first direction, in this embodiment clockwise (power is provided to the motor 58 causing rotation of the rotating bristle assembly 50). When activator slide 24 is in a second position (i.e., when activator slide 24 is fully slid towards a second end 30 of the channel 26), the electric toothbrush 10 is in a second "on" position and the cylindrical rotating bristle assembly 50 rotates in a second direction, in this embodiment counterclockwise (power is provided to the motor 58 causing rotation of the rotating bristle assembly 50). When activator slide 24 is in an intermediate position (i.e., when activator slide 24 is slid to an intermediate position between the first end 28 and the second end 30 of the channel 26), the toothbrush 10 is an "off" position (power is not provided to the motor 58).

It is, of course, within the scope of the invention to use alternate means of switching the toothbrush 10 from "on" to "off", etc., such as a water-proof single press button with various stages, or a plurality of water proof individual push buttons with independent and discrete functions. FIGS. 1C and 1D illustrate a preferred waterproof push-button embodiment of a power switch 124 suitable for use with the present invention. Switch 124 comprises two buttons 126, 128 configured to turn the toothbrush "on" and "off" and/or to control the rotational direction (clockwise or counterclockwise) of the rotating bristle assembly 50 during operation. For example, the top button 126 can turn the motor on, causing the bristle assembly 50 to rotate, while the bottom button 128 can turn the motor off, causing the bristle assembly to stop rotating. For another example, the top button 126 can turn the motor on causing the bristle assembly 50 to rotate clockwise, while the bottom button 128 can turn the motor on causing the bristle assembly to rotate counterclockwise. For another example, pushing the top button 126 once can turn the motor on, causing the bristle assembly 50 to rotate clockwise, pushing the top button 126 twice can turn the motor on, causing the bristle assembly 50 to rotate counterclockwise, while the bottom button 128 can turn the motor off, causing the bristle assembly to stop rotating. As can be seen, various configurations can be used for the push buttons such that the bristle assembly 50 can be caused to rotate in a desired direction, or stopped, all of which are within the purview of those of ordinary skill in the art.

The activator slide 24 or switch 124 can be located anywhere on the handle body 12. As shown in FIGS. 1A and 1B, the activator slide 24 or switch 124 is on the rear of the handle body 12, namely, the side of the handle body 12 opposite the direction the bristle assembly 50 is facing. Alternatively, the activator slide 24 or switch 124 can be located on the front of the handle body 12, such as directly below the exposed bristles of the bristle assembly 50, or on a side of the handle body 12.

The outer surface 20 of the handle body 12 may be formed of, or comprised of, or coated with, a "squeezable" or compressible material that deflects slightly when a gripping force is applied. Such a construction makes the toothbrush 10 more comfortable to hold and, therefore, easier to use. Optionally, the handle body 12 may be formed in a double-sided configuration with an elongate flat portion 22b antipodal to, or at any other angle relative to, the flat portion 22a. Alternatively, the outer surface 20 of the handle body 12 also may comprise grips, ridges, bumps, surface features, and/or surface textures (not depicted in the figures) to facilitate a user firmly grasping the handle body 12, particularly, when the handle body 12 is wet. Further preferred enhancements include grips, surface features, and/or surface textures that are aesthetically pleasing in appearance, although any number, shape, structure, and/or configuration may be included. As such, the provision of the outer surface 20 allows the user of the toothbrush 10 to appropriately brush the gums and all the tooth surfaces while essentially maintaining the same grip on the handle body 12. Simple adjustments are possible for the user via slight movement of the wrist and a switch in the rotational direction of the rotating bristle assembly 50.

A rotating ring 15 can be attached to the top portion of the handle body 12 as an illustrative attachment mechanism between the stem 14, if removable, and the handle body 12. For example, the rotating ring 15 is configured to detachably receive the stem 14 at the end opposite the head 40. The rotating ring 15 preferably has a fixed portion which is secured to the handle body 12, and a rotating portion designed to be turned in either a clockwise or counterclockwise direction. The rotating ring 15 has a threaded outer surface 32 (best seen in FIG. 5) complementary of a corresponding threaded inner surface 16 on the stem 14, at the end opposite the head 40 (best seen in FIGS. 4A-4B). The rotating ring 15, therefore, is configured to thread the stem 14 onto the handle body 12 (best seen in FIG. 3) such that the stem is rigidly retained by the handle body 12, and such that stem 14 is mechanically engaged with the rotation means of the electric toothbrush 10. It is envisioned that the rotating ring 15 may be a part of the stem 14 and, therefore, the system described would be reversed relative to the handle body 12 and the stem 14. Alternatively, another attachment mechanism between the stem 14 and the handle body 12 can be a snap fit or cooperating clips.

The handle body 12 comprises an internal cavity 52 (best seen schematically in FIG. 5) that houses a rotation means configured to drive rotation of the rotating bristle assembly 50. The rotation means includes a battery 56 and a motor 58 that the battery 56 powers. The battery 56 is accessible from a snap lid 100 on the bottom of the handle body 12 (best seen in FIG. 2B). The rotation means further includes a drive axle 60, which is operatively connected to and powered by motor 58 on a first side, and a splined cylindrical mandrel 61, which is attached to and rotated about its longitudinal axis by the motor 58 rotating the drive axle 60. The splined cylindrical mandrel 61 is on the side opposite the drive axle 60. The inner surface 60 of the splined cylindrical mandrel 61 defines a series of complementary splines configured to mechanically engage with a portion of the stem 14. As such, when the stem 14 is attached to the handle body 12, and when the motor 58 rotates the drive axle 60, the cylindrical mandrel 61 also rotates and transmits the rotation through the stem 14 to the rotating bristle assembly 50. FIG. 5 is an illustrative schematic of such a drive mechanism and attachment means, both of which are within the purview of those of ordinary skill in the art.

It is envisioned that various other configurations and structures are possible for the rotation means of the toothbrush 10. For example, a clutch configuration or other frictional transmission configuration, a tongue and groove configuration, a hex key and slot configuration all are suitable alternatives. For another example, in the non-interchangeable stem configuration, the drive axle 60 can connect directly to the bristle axle 17 and/or the drive axle 60 and the bristle axle 17 can be the same component extending from the motor 58 to the rotating bristle assembly 50.

Referring now to FIGS. 4A and 4B, the interchangeable stem 14 comprises, at one end, a head 40 with a rotating bristle assembly 50 and a bristle guard 18, and, extending down from the head 40, a thinner neck 42 (best seen in FIGS. 1A and 1B). The neck 42 is elongate so as to allow the head 40 to extend deep into a user's mouth. The neck 42 is terminated in this particular embodiment with the threaded inner surface 16 configured, at least in part, to cooperate with the rotating ring 15 as the attachment means to the handle body 12. Generally speaking, the non-interchangeable stem 14 has a configuration analogous to the interchangeable stem 14, with the main exception that the non-interchangeable stem 14 does not have a rotation disc 13 or a threaded inner surface 16, the elongate neck 42 simply being permanently attached to the top of the handle body 12.

The neck 42 of the stem 14 is generally a hollow cylinder having a generally cylindrical outer wall 82 defining an elongate cylindrical passage 84 therethrough extending from the base proximal to the handle body 12 to the bristle guard 18. The elongate cylindrical passage 84 extends from the bottom of the neck 42 (where the complementary threading 16 is situated) to the top of the neck 42 (where the rotating bristle assembly 50 and the bristle guard 18 are situated). A bristle axle 17 extends through the elongate cylindrical passage 84 of the neck 42 and engages with the rotating bristle assembly 50 such that when the bristle axle 17 is rotated about its longitudinal axis by the rotation means of the handle 14, the rotating bristle assembly 50 also rotates about its longitudinal axis. Depending on the direction of rotation of the rotations means, the rotating bristle assembly 50 is configured to rotate clockwise or counterclockwise.

The rotating bristle assembly 50 of the stem 14 also may be configured to rotate about a fixed or variable axis. For example, as the rotating bristle assembly 50 rotates, the rotating bristle assembly 50 may move towards or away from the longitudinal axis of the toothbrush 10. As such, not only is the rotating bristle assembly 50 configured to brush, sweep, and swipe, clockwise or counterclockwise, in a direction about the longitudinal axis of the toothbrush 10, the rotating bristle assembly 50 also may be configured to variably press harder or softer against a stationary adjacent oral surface during operation.

The bristle guard 18 of the stem 14 extends from above one end of the rotating bristle assembly 50, namely the top end 86, partially over the extended bristles 53, to the junction of the head 40 with the neck 42 (best seen in FIGS. 1B and 4A-4B). The bristle guard 18 is contiguous with the outer cylindrical wall 82 of the neck 42 (i.e., they substantially share a contiguous outer surface, but are not necessarily co-cylindrical). At the end of the bristle guard 18 opposite the neck 42, the bristle axle 17, which is extending through the rotating bristle assembly 50, engages to and rotatably pivots relative to the bristle guard 18. As such, the bristle guard 18 is not merely hanging over the rotating bristle assembly 50, but instead the bristle guard 18 is retained in place by the bristle axle 17, which is journaled into the top end 86 of the bristle guard 18. Therefore, when the rotating bristle assembly 50 is rotating, the rotating bristle assembly 50 is bounded, at least partially, by the bristle guard 18 above (best seen in FIGS. 4A-4B), by the bristle guard 18 to the side, and by the neck 42 below.

It is envisioned that the width of the bristle guard 18 may take various dimensions. Preferably, however, the width of the bristle guard 18 extends from a quarter (or approximately a quarter) to half-way (or approximately halfway) around the rotating bristle assembly 50. Additionally, it is envisioned that the structure of the bristle guard 18 may take more complex configurations for additional functionality. Moreover, the outer surface 19 of the bristle guard 18 may comprise a raised surface texture and/or surface feature. The outer surface 19 of the bristle guard 18, therefore, may be configured to provide a firm textured surface with which a user may clean or massage or stimulate his or her tongue, cheeks, and/or gums. The outer surface 19 of the bristle guard 18 also may be used as a scaling tool for more abrasive cleaning of an oral surface, should the rotating bristle assembly 50 not provide enough cleaning power.

In one embodiment, the outer cylindrical wall 82 of the neck 42 of the stem 14, along with the bristle guard 18 contiguous thereto, may be incrementally rotatable. Said another way, when the stem 14 is attached to the handle body 12, the outer cylindrical wall 82 of the neck 42 with the bristle guard 18 may be rotatable about the longitudinal axis of the toothbrush 10. Therefore, the alignment of the bristle guard 18, relative to any point along the outer circumference of the handle body 12, may be variable. As such, the bristle guard 18 can be configured to rotate in increments around the rotating bristle assembly 50 so as to change whether the bristle guard 18 is on the right side of the rotating bristle assembly 50, whether the bristle guard 18 is aligned with the activator slide 24, whether the bristle guard 18 is antipodal relative to the activator slide 24, or whether the bristle guard 18 is on the left side of the rotating bristle assembly 50, etc.

In the interchangeable embodiment, the bristle axle 17, which extends through the elongate cylindrical passage 84 of the neck 42, comprises a plurality of complementary splines 44 (best seen in FIGS. 4A-4B). The plurality of complementary splines 44 of the bristle axle 17 of the stem 14 are configured to engage with the series of cooperating splines along the inner surface 60 of the splined cylindrical mandrel 61 of the handle body 12. As such, when the stem 14 is attached to the handle body 12, and when the motor 58 rotates the drive axle 60, the cylindrical mandrel 61 also rotates and transmits the rotation through its splines 60 to the plurality of complementary splines 44 of the bristle axle 17 and up to the rotating bristle assembly 50. Therefore, when the bristle axle 17 is rotated about its longitudinal axis by the rotation means of the handle 14, the rotating bristle assembly 50 also rotates about its longitudinal axis. This feature also can be present in the non-interchangeable embodiment of the toothbrush 10 of a singular bristle axle 17/drive axle 60 configuration is used.

Referring now to FIG. 4B, in this embodiment, the interchangeable stem 14 is configured such that the bristle axle 17, attached to the rotating bristle assembly 50, is separable from the rest of the interchangeable stem 14. More specifically, the bristle axle 17 is configured to detachably extend through the elongate cylindrical passage 84 from the bottom of the neck 42 (where the complementary threading 16 is situated) to the top of the neck 42 (where the rotating bristle assembly 50 and the bristle guard 18 are situated). The bristle axle 17 can be pulled out from the elongate cylindrical passage 84 which, in turn, also pulls out the rotating bristle assembly 50. In this way, the second embodiment of the interchangeable stem 14 can have a separately replaceable bristle axle 17 with attached new rotating bristle assembly 50. This allows a user to replace the bristles 53 or bristle assembly 50 and the attached bristle axle 17 without having to replace the rest of the interchangeable stem 14. Stop 130 prevents the bristle assembly 50 and bristle axle 17 from being forced too far into the cylindrical passage 84, thus helping to prevent damage to the assembly.

Referring now to FIGS. 6-9, the toothbrush is shown in use, and illustrates a preferred method for using an electric toothbrush of the present invention and a preferred method of brushing a user's teeth and gums according to the invention. FIG. 6 is a perspective view of the electric toothbrush of FIG. 1 operating on the outside facing surfaces of teeth and gums on the upper right side, or the lower left side, of a user's jaw. FIG. 7 is a perspective view of the electric toothbrush of FIG. 1 operating on the outside facing surfaces of teeth and gums on the upper left side, or the lower right side, of a user's jaw. FIG. 8 is a perspective view of the electric toothbrush of FIG. 1 operating on the inside facing surfaces of teeth and gums on the upper right side, or the lower left side, of a user's jaw. FIG. 9 is a perspective view of the electric toothbrush of FIG. 1 operating on the inside facing surfaces of teeth and gums on the upper left side, or the lower right side, of a user's jaw.

In FIGS. 6 and 9, the rotating bristle assembly 50 is indicated by the rotation arrow as spinning in a first direction and in FIGS. 7 and 8, the rotating bristle assembly 50 is indicated by the rotation arrow as spinning in a second direction opposite the rotation of the first direction. More specifically, and as disclosed in more detail below, the rotating bristle assembly 50 should be activated by the user to rotate in a direction such that the bristles 53 always rotate in a direction from the gum towards the tooth crown surface, namely in the direction of gum growth, so as to prevent forcing the gums up and away from the tooth and to prevent forcing debris under the gum between the gum and the tooth surface. Thus, while the rotating bristle assembly 50 can spin in either direction when in use, the preferred direction of rotation is in a direction such that the bristles 53 rotate in a direction from the gum towards the tooth crown surface.

One exemplary method for using the toothbrush 10 and for brushing the teeth and gums using the preferred embodiments of the toothbrush 10 is as follows. A user grasps the handle 14 of the toothbrush 10 along the outer surface 20. The user positions the handle 14 in the user's grasp such that the user comfortably and easily engages with the activator slide 24 or switch 124. The user can use any physical means within its grasp to engage with the activator slide 24 or switch 124. In the interchangeable embodiment, if the user's personal stem 14 is not already attached to the handle body 12, the user then attaches the user's personal stem 14 to the handle body 12. In the non-interchangeable embodiment, the stem 14 is already permanently attached to the handle body 12.

More specifically, in a preferred embodiment of the interchangeable embodiment, the user maneuvers the interchangeable stem 14 (splined end of the bristle axle 17 leading) towards the rotating ring 15 of the handle body 12. The user inserts the bristle axle 17 through an opening defined in the top end of the handle body 12 such that the plurality of splines 44 extends through the internal cavity 52 of the handle towards the rotation means. The user continues to insert the bristle axle 17 such that the plurality of splines 44 extend into the splined cylindrical mandrel 61 and engage with the series of complementary splines 60 along its internal surface.

In an embodiment with a screw-thread attachment means, the user then screw threads the stem 14 to the handle body 12 via the rotating portion of the rotating ring 15. The fixed portion of the rotating ring 15 remains secured to the handle body 12, which forces the threaded outer surface 32 of the rotating ring 15 to engage with the complementary threaded inner surface 16 of the stem 14. As such, the stem 14 is rigidly retained by the handle body 12, and the stem 14 is correctly and fully engaged with the rotation means of the toothbrush 10.

With the goal of first cleaning the upper right facial (outer) side and then the lower left facial side, the user slides the activator slide 24 or presses switch 124 to an "on" position that drives counterclockwise rotation of the rotating bristle assembly 50 of the stem 14 whereby when the rotating bristle assembly 50 is inserted into the mouth, the bristles 53 of the rotating bristle assembly 50 rotate in a direction from the gums towards the crown surface of the tooth or teeth to which the rotating bristle assembly 50 is being applied. More specifically, the battery 56 powers the motor 58, which drives rotation of the drive axle 60, which in turn drives rotation of the splined cylindrical mandrel 61, which in turn drives rotations of the bristle axle 17 which in turn drives rotation of the bristle assembly 50.

The user then maneuvers the stem 14 of the electric toothbrush 10 into the user's mouth towards the upper right facial side of the jaw 70. The user applies the rotating bristle assembly 50 to the teeth and gums starting along the gingival margin and works from the gums towards the tooth crown whereby the bristles 53 of the rotating bristle assembly 50 rotate in a direction from the gums towards the crown surface of the tooth or teeth to which the rotating bristle assembly 50 is being applied. The user does this to every tooth and the gums in the upper right facial side of the jaw 70.

When the user finishes brushing the upper right facial side of the jaw 70, the user makes a series of comfortable and easy wrist movements and is in a position to brush the teeth and gums on the lower left facial side of the jaw 70. More specifically, the user rotates the toothbrush approximately 180 degrees, which puts the toothbrush 10 in a more or less proper position for brushing the teeth and gums on the lower left facial side of the jaw 70. The user then maneuvers the stem 14 of the toothbrush 10 towards the lower left facial side of the jaw 70. The user applies the rotating bristle assembly 50 to the teeth and gums starting along the gingival margin and works from the gums towards the tooth crown. The user does this to every tooth and the gums in the lower left facial side of the jaw 70.

Then, with the goal of cleaning the upper left facial side and the lower right facial side, the user slides the activator slide 24 or presses the switch 124 to an "on" position that drives clockwise rotation of the rotating bristle assembly 50 of the stem 14 whereby when the rotating bristle assembly 50 is inserted into the mouth, the bristles 53 of the rotating bristle assembly 50 rotate in a direction from the gums towards the crown surface of the tooth or teeth to which the rotating bristle assembly 50 is being applied.

The user then maneuvers the stem 14 of the toothbrush 10 towards the upper left facial side of the jaw 70. The user applies the rotating bristle assembly 50 to the teeth and gums starting along the gingival margin and works from the gums towards the tooth crown whereby the bristles 53 of the rotating bristle assembly 50 rotate in a direction from the gums towards the crown surface of the tooth or teeth to which the rotating bristle assembly 50 is being applied. The user does this to every tooth and the gums in the upper left facial side of the jaw 70.

When the user finishes brushing the upper left facial side of the jaw 70, the user makes a series of comfortable and easy wrist movements and is in a position to brush the teeth and gums on the lower right facial side of the jaw 70. More specifically, the user rotates the toothbrush approximately 180 degrees, which puts the toothbrush 10 in a more or less proper position for brushing the teeth and gums on the lower right facial side of the jaw 70. The user then maneuvers the stem 14 of the toothbrush 10 towards the lower right facial side of the jaw 70. The user applies the rotating bristle assembly 50 to the teeth and gums starting along the gingival margin and works from the gums towards the tooth crown whereby the bristles 53 of the rotating bristle assembly 50 rotate in a direction from the gums towards the crown surface of the tooth or teeth to which the rotating bristle assembly 50 is being applied. The user does this to every tooth and the gums in the lower right facial side of the jaw 70.

Then, with the goal of cleaning the upper right lingual (inner) side and the lower left lingual side (best seen in FIG. 8), the user again makes a series of comfortable and easy wrist movements and maneuvers the stem 14 towards the upper right lingual side of the jaw 70. The user applies the rotating bristle assembly 50 to the teeth and gums starting along the gingival margin and works from the gums towards the tooth crown whereby the bristles 53 of the rotating bristle assembly 50 rotate in a direction from the gums towards the crown surface of the tooth or teeth to which the rotating bristle assembly 50 is being applied. The user does this to every tooth and the gums in the upper right lingual side of its jaw 70.

When the user finishes brushing the upper right lingual side of the jaw 70, the user again makes a series of comfortable and easy wrist movements and maneuvers the stem 14 towards the lower left lingual side. The user applies the rotating bristle assembly 50 to the teeth and gums starting along the gingival margin and works from the gums towards the tooth crown whereby the bristles 53 of the rotating bristle assembly 50 rotate in a direction from the gums towards the crown surface of the tooth or teeth to which the rotating bristle assembly 50 is being applied. The user does this to every tooth and the gums in the lower left lingual side of its jaw 70.

Then, with the goal of cleaning the upper left lingual side and the lower right lingual side, the user slides the activator slide 24 or presses the switch 124 of the handle body 12 to an "on" position that drives counterclockwise rotation of the rotating bristle assembly 50 of the stem 14 whereby when the rotating bristle assembly 50 is inserted into the mouth, the bristles 53 of the rotating bristle assembly 50 rotate in a direction from the gums towards the crown surface of the tooth or teeth to which the rotating bristle assembly 50 is being applied.

The user then maneuvers the stem 14 of the toothbrush 10 towards the upper left facial side of the jaw 70. The user applies the rotating bristle assembly 50 to the teeth and gums starting along the gingival margin and works from the gums towards the tooth crown whereby the bristles 53 of the rotating bristle assembly 50 rotate in a direction from the gums towards the crown surface of the tooth or teeth to which the rotating bristle assembly 50 is being applied. The user does this to every tooth and the gums in the upper left facial side of its jaw 70.

When the user finishes brushing the upper left lingual side of the jaw 70, the user again makes a series of comfortable and easy wrist movements and maneuvers the stem 14 towards the lower right lingual side. The user applies the rotating bristle assembly 50 to the teeth and gums starting along the gingival margin and works from the gums towards the tooth crown whereby the bristles 53 of the rotating bristle assembly 50 rotate in a direction from the gums towards the crown surface of the tooth or teeth to which the rotating bristle assembly 50 is being applied. The user does this to every tooth and the gums in the lower right lingual side of the jaw 70.

Then, the user can brush the outer and inner surfaces of the front top and bottom teeth and the gums in much the same manner, taking care to have the rotating bristle assembly 50 rotating in the proper direction from the gums towards the tooth crown. Finally, the user can brush the biting occlusal surfaces of the teeth, specifically the occlusal surfaces of the molars, using the rotating bristle assembly 17 in either the clockwise or counterclockwise direction as no contact with the gums is involved.

Having brushed the gums and all of the tooth surfaces, while essentially maintaining the same grip on the handle body 12 and generally only having to use one arm, the user slides the activator slide 24 of the handle body 12 to the intermediate position or presses the switch 124 to an "off" position. This turns "off" the electric toothbrush, which stops rotation of the rotating bristle assembly 50 of the stem 14.

In this manner, the user has operated the toothbrush 10 so as to always have the rotating bristle assembly 50 rotate in a direction from the gums towards the tooth crown, thereby brushing in the direction off gum growth. This prevents the bristles 53 from lifting the gums away from the teeth, from loosening the gums, and from forcing debris under the gums (between the gums and the teeth). This is a preferred method of brushing that is more healthful to the gums and therefore results in better oral hygiene.

If the toothbrush 10 is provided with a suitable outer surface to the bristle guard 18, and if the user desires to brush the tongue, inner cheeks, or gums, the user then can make a series of comfortable and easy wrist movements to rotate the bristle guard 18 to face the tongue, inner cheek, or gums. The user then maneuvers the stem 14 towards the tongue, inner cheek, or gums and scrubs the tongue, inner cheek, or gums with the outer surface 19 of the bristle guard 18. The user preferably does this to the entire surface of the tongue, inner cheek, and/or gums. Having brushed the entire oral cavity, while essentially maintaining the same grip on the handle body 12, the user removes the stem 14 of the toothbrush 10 out of the mouth and places the toothbrush 10 down.

Referring now to FIGS. 10A and 10B, an embodiment of the toothbrush 10 of the present invention may comprise a second embodiment of a handle body 12 and a bristle shield 200. FIG. 10A shows an embodiment of the toothbrush 10 with an activator slide 24 switch, and FIG. 10B shows an embodiment of the toothbrush with a push button switch 124. The second embodiment of the handle body 12 comprises a knurled threaded cap 300 instead of the snap fit lid 100 to access the battery 52. The knurled threaded cap 300 is configured to be water-tight and easy to open.

The bristle shield 200 is configured as an elongate cylindrical domed cap that simply goes over and surrounds the interchangeable stem 14. The interchangeable stem 14 would be inserted into the interior spaced defined by the elongate cylindrical domed cap 200. The end rim of the bristle shield 200 press-fits up against the end of the handle body 12, proximate to the interchangeable stem 14, and securely engages onto the handle body 12. It is envisioned that the end of the handle body 12 proximate to the interchangeable stem 14 may be slightly tapered and/or surfaced textured to facilitate and improve the press-fit with the rim of the bristle shield 200.

As such, the bristle shield 200 provides a built-in feature for additional protection against bristle-introduced infections to the periodontium as the bristles 53 can be shield from the bathroom air. Moreover, as the bristle shield 200 extends out around the previously unbound portion of the bristles 53, the bristles shield 200 allows sufficient air around the bristles 53 so as to appropriately dry between tooth and gum brushings.

Referring now to FIGS. 11A, 11B, 11C, and 12, exemplary embodiments of the electric toothbrush of the present invention is video capable. The video capable embodiment is generally identical to the electric toothbrush embodiment of FIGS. 10A and 10B except for the following description. In FIGS. 11A-11C, the camera device 500 is shown located on and/or attached to the handle body 12. In FIG. 12, an alternate embodiment is shown in which the camera device 500 is shown located on and/or attached to the stem 14.

The video capable embodiment comprises a handle body 12, defining a cylindrical body, and an interchangeable stem 14, having a head 40 with a rotating bristle assembly 50. The video capable embodiment also comprises a bristle shield 200 defining an elongate cylindrical domed cap for the interchangeable stem 14. The video capable embodiment also comprises a camera device 500 communicatively coupled, via a pathway 600, to a user useful display 700. In this way, the video capable embodiment is configured to provide a user with live intraoral video obtained during operation of the electric toothbrush.

The handle body 12 comprises a switch means for activating and deactivating 24, 124 (turning on and off) an internal motor 58, a battery 56, electrical components for powering the rotating bristle assembly 50, and a knurled threaded cap 300 to access the battery 56 and/or any other internal components. The handle body 12 is configured to provide a suitable handgrip for a user about the cylindrical body. The cylindrical body also defines a means for detachably engaging 400 the camera device 500 to an exterior side of the electric toothbrush.

In the exemplary embodiments of FIGS. 11A, 11B, 11C, and 12 the means for detachably engaging 400 is a two part press fit system (400A and 400B) configured to tightly receive the camera device 500. The camera device 500 may be rigidly but removably retained between the means for detachably engaging 400A and 400B such that a user gripping the handle body 12 does not obstruct a video feed of his or her gingival margin while using the electric toothbrush 10. As the appropriate daily brushing accomplished by the electric toothbrush 10 requires minimal toothpaste (and the foam created therefrom), the video capable embodiment is characterized by unobstructed video imaging. Moreover, the means for detachably engaging 400A and 400B is substantially antipodal to the switch means 24, 124; although, various positions about the exterior of the handle body 14 are envisioned. More specifically, the camera device 500 and the switching means 24, 124, can be placed at any point on the handle body 12, with the switching means 24, 124 preferably on the back side of the handle body 12, and the camera device 500 preferably on the front side of the handle body 12. This places the switching means 24, 124 out of the way of the camera device 500, and allows the camera device 500 to have a generally unobstructed view into the user's mouth.

In certain exemplary embodiments, the means for detachably engaging 400 may be an integral part of the handle body 12 or may be a separate and distinct component attached thereto. Moreover, the means for detachably engaging 400 is not limited to positioning on and/or orientation relative to the handle body 12. A person having ordinary skill in the art understands that the means for detachably engaging 400 may be part of/attached to the interchangeable stem 14 or any other component of the electric toothbrush 10.

Moreover, the means for detachably engaging 400 may be larger or smaller and structured according to the embodiments of the camera device 500. In this way, the means for detachably engaging 400 may be structured to complement and/or conform to the camera device 500. Moreover, the means for detachably engaging 400 is not limited to a friction fit engagement. A person having ordinary skill in the art understands that the means for detachably engaging 400 may incorporate magnets, clips, protrusions, surface features, etc. for retaining the camera device 500 in position, alignment, and orientation.

In the exemplary embodiments of FIGS. 11A, 11B, 11C, and 12 the camera device 500 is a flexible borescope optical device consisting of a flexible conductive cable (optionally, tubular), a lens, a camera sensor, a light mechanism, and a relay optical system as is understood by a person having ordinary skill in the art. The aperture and lighting mechanism of the camera device 500, when detachably engaged to the handle body 14, is aimed towards the oral cavity of a user so as to capture intraoral video. The intraoral video is then transmitted, via the pathway 600, to the user useful display 700. The lighting mechanism can be individual LED lights surrounding the aperture of the camera device 500; although, other lighting mechanisms known to a person having ordinary skill in the art are envisioned.

In certain exemplary embodiments, the camera device 500 may be a Depstech™ Micro USB borescope waterproof inspection camera or any other equivalent device known to a person having ordinary skill in the art. For these embodiments, the flexible tube or tubular conductive cable is the pathway 600 communicatively coupling the camera device 500 to the user useful display 700. The camera device 500 is not limited to this specific borescope embodiment. A person having ordinary skill in the art understands that the camera device may include many variations and combinations of articulation mechanism components, ranges of articulation, fields of view, and angles of view as well as any known and applicable objective lens and/or digital camera sensors. Moreover, the camera device 500 may include 10,000 pixels to 22,000 pixels. Moreover, the camera device 500 may be configured for 640×480 resolution, or upwards of 4K HD video, or any other video capture capability known to a person having ordinary skill in the art.

In certain exemplary embodiments, the camera device 500 may be a self-contained optical device comprising a power source, wiring, electronic boards and circuitry, system bus, and/or means for capturing, processing, and/or transmitting video data for use, directly or indirectly, by a user. In this way, the camera device 500 may be configured to capture, process, and transmit an intraoral video feed, via a USB/power cable 600, to a user useful display 700. The user useful display 700 may be a 3-inch LCD display with 320×240 pixels or better, or any other equivalent or upgraded embodiment known to a person having ordinary skill in the art.

Moreover, the camera device 500 may be a multi-component system having the components and means for processing and/or transmitting video data spread out across the electric toothbrush 10. For example, in one exemplary embodiment, the power source, electronic boards/circuitry, system bus, and means for capturing, processing, and/or transmitting video data is housed within the handle body 14 and/or the user useful display 700.

In another exemplary embodiment, the system components may be spread out between the camera device 500 and the user useful display 700. In these embodiments, the camera device 500 may be configured to capture a video feed and/or partially process the video feed for transmission via a wireless communications pathway 600 to the user useful display 700. A person having ordinary skill understands that the wireless communications pathway 600 may be Bluetooth® enabled, cellular telecommunications network enabled, Wi-Fi® enabled, etc. The user useful display 700 also may be configured to receive and/or partially process the video feed for display to the user. A person having ordinary skill understands that the user useful display 700 may be a portable computing device, such as a smart phone, configured to process video data, decrease video distortion, and/or improve video quality. For example, in one exemplary embodiment, the user useful display 700 is an USB OTG (on-the-go) compatible Android® smartphone; however, many other similar devices are envisioned.

The electric toothbrush for proper periodontium prophylaxis can be marketed in a kit form with a single handle body 12 and a plurality of interchangeable stems 14. The various stems 14 can thus be replacements, specific task oriented shapes and/or stiffness, or individually assigned to different members of a family. Color distinction and firmness are thus often characteristics of the different heads in a kit. Although handle body 12 is discussed as preferably battery powered, of course, the invention also includes other well-known power supplies such as corded for outlet connection or rechargeable batteries and an associated brush holder/charger.

Thus, it can be seen that the toothbrush 10 and the method for using the toothbrush 10 is configured to effectively and efficiently remove plaque and debris from the user's teeth while protecting and preserving a user's gingival margin and periodontium by recreating a proper tooth and gum brushing procedure and preventing a loosening of a user's gums, thus increasing the overall health of a user's gums and teeth. As described herein, the toothbrush 10 has a brush geometry, a rotating bristle assembly 50, and a reversible rotational direction so as to implement a proper brushing technique having the bristles 53 rotate in the direction of gum growth from the gum towards the crown of the tooth, and regardless of the specific tooth or teeth being brushed, the toothbrush 10 is configured to brush the gums and teeth in the direction of gum growth so as to not loosen the gums and to improve gum health.

Although the particular embodiments shown and described above will prove to be useful in many applications in the electric toothbrush art to which the present invention pertains, further modifications of the present invention will occur to persons skilled in the art. All such modifications are deemed to be within the scope and spirit of the present invention as defined by the appended claims.

What is claimed is:

1. A toothbrush comprising:
   a) a handle body for manual engagement by a user with one hand;
   b) a stem comprising an elongate neck;
   c) a head having a rotating bristle assembly comprising bristles;
   d) a means for rotating the rotating bristle assembly, the handle body comprising the means for rotating the rotating bristle assembly;
   e) a bristle guard; and
   f) an attached camera device,
   wherein the means for rotating the rotating bristle assembly is powered and the rotating bristle assembly is selectably motorized to rotate in a first direction and a second direction, the second direction being opposite to the first direction,
   wherein upon activating the means for rotating the rotating bristle assembly such that the rotating bristle assembly is spinning in the first direction and upon applying the rotating bristle assembly to a first grouping of a user's teeth, the bristles rotating in the first direction engage at least one of the user's gums and the user's teeth and rotate in a direction from a user's gums towards crowns of the user's teeth, and
   wherein upon activating the means for rotating the rotating bristle assembly such that the rotating bristle assembly is spinning in the second direction and upon applying the rotating bristle assembly to a second grouping of the user's teeth, the bristles rotating in the second direction engage at least one of the user's gums and the user's teeth and rotate in a direction from the user's gums towards crowns of the user's teeth,
   whereby the toothbrush is configured to effectively and efficiently remove debris from the user's teeth whereby the bristles do not lift or loosen the user's gums from the user's teeth or force debris between the user's gums and the user's teeth, thereby not adversely affecting the user's gum health,
   the means for rotating the rotating bristle assembly comprises a bristle axle mechanically engaged with the rotating bristle assembly, the bristle axle extending through the elongate neck, the bristle axle configured to rotate the rotating bristle assembly in the first direction and in the second direction,
   wherein the bristle guard comprises a bristle-facing side and a non-bristle facing side, the non-bristle facing side defining a raised surface texture or raised surface feature that is configured for tongue and cheek cleaning, and
   wherein the camera device is positioned on the handle body and aimed along a longitudinal axis of the handle towards the rotating bristle assembly so as to capture a visual field about the rotating bristle assembly.

2. The toothbrush of claim 1, wherein the stem is detachable from the handle.

3. The toothbrush of claim 1, further comprising:
   a) a video display; and
   b) the camera device is communicatively coupled, via a communications pathway, to the video display, the camera device configured to capture and transmit an intraoral video feed for display at the video display,
   wherein the video display is remote from an assembly of the handle body, the interchangeable stem, and the camera.

4. The electric toothbrush of claim 3, wherein the video display comprises electronic boards and circuitry for receiving and at least partially processing the intraoral video feed transmitted by the camera device.

5. The electric toothbrush of claim 4, wherein the video display is at least one of a portable computing device and a smartphone.

6. The electric toothbrush of claim 3, wherein the camera device defines an aperture and comprises a lens, a digital camera sensor, a lighting mechanism, and a relay optical system, the camera device having a video capture capability.

7. The electric toothbrush of claim 6, wherein the lighting mechanism comprises one or more individual light emitting diodes positioned proximate to the aperture so as to illuminate the visual field about the rotating bristle assembly.

8. The electric toothbrush of claim 3, wherein the handle body defines a means for detachably engaging the camera device to an exterior side of the handle body so as to position and aim the camera device towards the visual field about the rotating bristle assembly.

9. The electric toothbrush of claim 3, wherein:
   the video display is integral to one of a portable computing device and a smartphone, the one of a portable computing device and a smartphone comprising electronic boards and circuitry for receiving and at least partially processing the intraoral video feed transmitted by a flexible borescope; and the flexible borescope comprises electronic boards and circuitry for transmitting and at least partially processing the intraoral video feed before transmitting the intraoral video feed to the video display.

10. A method for implementing a proper tooth and gum brushing technique comprising:
   a) supplying a toothbrush comprising a handle body and a stem comprising an elongate neck, a head having a rotating bristle assembly comprising bristles, a means for rotating the rotating bristle assembly, a bristle guard, and a camera device, wherein the means for rotating the rotating bristle assembly is powered and the rotating bristle assembly is selectably motorized to rotate in a first direction and a second direction, the second direction being opposite to the first direction
   b) activating the means for rotating the rotating bristle assembly such that the rotating bristle assembly is spinning in the first direction and applying the rotating bristle assembly to a first grouping of a user's teeth whereby the bristles rotating in the first direction engage at least one of the user's gums and the user's teeth and rotate in a direction from a user's gums towards crowns of the user's teeth;
   c) activating the means for rotating the rotating bristle assembly such that the rotating bristle assembly is spinning in the second direction and applying the rotating bristle assembly to a second grouping of the user's teeth whereby the bristles rotating in the second direction engage at least one of the user's gums and the user's teeth and rotate in a direction from the user's gums towards crowns of the user's teeth;
   d) positioning the camera device on the handle body and aiming the camera device along a longitudinal axis of the handle towards the rotating bristle assembly so as to capture a visual field about the rotating bristle assembly; and
   e) communicatively coupling the camera device, via a communications pathway, to a video display, the camera device being configured to capture and transmit an intraoral video feed for display at the video display,
   whereby the electric toothbrush system is configured to effectively and efficiently remove debris from the user's teeth whereby the bristles do not lift or loosen the user's gums from the user's teeth or force debris between the user's gums and the user's teeth, thereby not adversely affecting the user's gum health.

11. The method of claim 10, wherein:
the handle body comprises the means for rotating the rotating bristle assembly; and
the means for rotating the rotating bristle assembly comprises a bristle axle mechanically engaged with the rotating bristle assembly, the bristle axle extending through the elongate neck, the bristle axle configured to rotate the rotating bristle assembly in the first direction and in the second direction.

12. The method of claim 11, wherein the bristle guard comprises a bristle-facing side and a non-bristle facing side, the non-bristle facing side defining a raised surface texture or raised surface feature that is configured for tongue and cheek cleaning.

13. The method of claim 10, wherein the stem is detachable from the handle.

14. A method of brushing a user's teeth with a toothbrush having a handle body and a stem comprising an elongate neck, a head having a rotating bristle assembly comprising bristles, a means for rotating the rotating bristle assembly, a bristle guard, and a camera device, wherein the means for rotating the rotating bristle assembly is powered and the rotating bristle assembly is selectably motorized to rotate in a first direction and a second direction, the second direction being opposite to the first direction, the method comprising the steps of:
   a) manually engaging the handle body with one hand;
   b) activating the means for rotating the rotating bristle assembly such that the rotating bristle assembly is spinning in the first direction and applying the rotating bristle assembly to a first grouping of a user's teeth whereby the bristles rotating in the first direction engage at least one of the user's gums and the user's teeth and rotate in a direction from a user's gums towards crowns of the user's teeth; and
   c) activating the means for rotating the rotating bristle assembly such that the rotating bristle assembly is spinning in the second direction and applying the rotating bristle assembly to a second grouping of the user's teeth whereby the bristles rotating in the second direction engage at least one of the user's gums and the user's teeth and rotate in a direction from the user's gums towards crowns of the user's teeth;
   d) positioning the camera device on the handle body and aiming the camera device along a longitudinal axis of the handle towards the rotating bristle assembly so as to capture a visual field about the rotating bristle assembly; and
   e) communicatively coupling the camera device, via a communications pathway, to a video display, the camera device being configured to capture and transmit an intraoral video feed for display at the video display,
   whereby the toothbrush is configured to effectively and efficiently remove debris from the user's teeth whereby the bristles do not lift or loosen the user's gums from the user's teeth or force debris between the user's gums and the user's teeth, thereby not adversely affecting the user's gum health.

15. The method of claim 14, wherein:
the handle body comprises the means for rotating the rotating bristle assembly; and
the means for rotating the rotating bristle assembly comprises a bristle axle mechanically engaged with the rotating bristle assembly, the bristle axle extending through the elongate neck, the bristle axle configured to rotate the rotating bristle assembly in the first direction and in the second direction.

\* \* \* \* \*